(12) United States Patent
Kuroda et al.

(10) Patent No.: US 8,597,294 B2
(45) Date of Patent: Dec. 3, 2013

(54) BIOLOGICAL TISSUE CLOSING DEVICE

(75) Inventors: Yasuyuki Kuroda, Hadano (JP);
Yukitoshi Kato, Hadano (JP)

(73) Assignee: Terumo Kabushiki Kaisha, Shibuya-Ku, Tokyo (JP)

( * ) Notice: Subject to any disclaimer, the term of this patent is extended or adjusted under 35 U.S.C. 154(b) by 1161 days.

(21) Appl. No.: 12/200,578

(22) Filed: Aug. 28, 2008

(65) Prior Publication Data

US 2009/0069810 A1 Mar. 12, 2009

Related U.S. Application Data

(60) Provisional application No. 60/976,110, filed on Sep. 28, 2007, provisional application No. 60/976,092, filed on Sep. 28, 2007.

(30) Foreign Application Priority Data

Aug. 28, 2007 (JP) ................. 2007-221898
Aug. 28, 2007 (JP) ................. 2007-221908

(51) Int. Cl.
*A61B 18/18* (2006.01)
*A61B 17/08* (2006.01)
*A61D 1/00* (2006.01)

(52) U.S. Cl.
USPC .......................................... 606/51; 606/213

(58) Field of Classification Search
USPC .............. 606/41–59, 213, 215; 607/118, 122
See application file for complete search history.

(56) References Cited

U.S. PATENT DOCUMENTS

| 5,507,744 A | 4/1996 | Tay et al. |
|---|---|---|
| 5,709,224 A | 1/1998 | Behl et al. |
| 5,810,810 A | 9/1998 | Tay et al. |
| 5,827,268 A | 10/1998 | Laufer |
| 5,919,200 A | 7/1999 | Stambaugh et al. |
| 6,004,316 A | 12/1999 | Laufer |
| 6,063,085 A | 5/2000 | Tay et al. |
| 6,077,261 A | 6/2000 | Behl et al. |
| 6,629,534 B1 | 10/2003 | St. Goar et al. |
| 6,752,813 B2 | 6/2004 | Goldfarb et al. |
| 6,939,348 B2 | 9/2005 | Malecki et al. |
| 7,165,552 B2 | 1/2007 | Deem et al. |
| 7,186,251 B2 | 3/2007 | Malecki et al. |
| 7,226,467 B2 | 6/2007 | Lucatero et al. |
| 7,257,450 B2 | 8/2007 | Auth et al. |

(Continued)

FOREIGN PATENT DOCUMENTS

| WO | WO 2004/086944 A2 | 10/2004 |
|---|---|---|
| WO | WO 2007/100067 A1 | 9/2007 |
| WO | WO 2008/073727 | 6/2008 |

*Primary Examiner* — Manuel Mendez
*Assistant Examiner* — Jenna Zhang
(74) *Attorney, Agent, or Firm* — Buchanan Ingersoll & Rooney PC

(57) ABSTRACT

A biological tissue closing device includes a clamper comprising a stick portion provided at a distal portion of a catheter for sticking to a biological tissue, and a sandwich member for sandwiching the biological tissue in cooperation with the stick portion, and an electric energy supply unit for supplying electric energy to the clamper. The biological tissue is fused by making the stick portion and the sandwich member of the clamper be electrode members, by sandwiching the biological tissue with the clamper and by supplying electric energy from the electric energy supply unit, wherein the clamper is configured so that each of the stick portion and the sandwich member are movable independently with respect to the catheter.

21 Claims, 13 Drawing Sheets

(56) References Cited

U.S. PATENT DOCUMENTS

| | | |
|---|---|---|
| 7,293,562 B2 | 11/2007 | Malecki et al. |
| 7,311,701 B2 | 12/2007 | Gifford et al. |
| 7,797,056 B2 | 9/2010 | Forde et al. |
| 8,021,359 B2 | 9/2011 | Auth et al. |
| 8,172,839 B2 * | 5/2012 | Kato .................................. 606/50 |
| 2004/0003819 A1 | 1/2004 | St. Goar et al. |
| 2004/0030382 A1 | 2/2004 | St. Goar et al. |
| 2004/0039442 A1 | 2/2004 | St. Goar et al. |
| 2004/0044350 A1 | 3/2004 | Martin et al. |
| 2004/0049207 A1 | 3/2004 | Goldfarb et al. |
| 2004/0092962 A1 | 5/2004 | Thornton et al. |
| 2004/0225300 A1 | 11/2004 | Goldfarb et al. |
| 2004/0230185 A1 * | 11/2004 | Malecki et al. ..................... 606/2 |
| 2004/0243122 A1 * | 12/2004 | Auth et al. ....................... 606/41 |
| 2004/0267191 A1 | 12/2004 | Gifford, III et al. |
| 2005/0021056 A1 | 1/2005 | St. Goar et al. |
| 2005/0021057 A1 | 1/2005 | St. Goar et al. |
| 2005/0033288 A1 * | 2/2005 | Auth et al. ....................... 606/49 |
| 2005/0033446 A1 | 2/2005 | Deem et al. |
| 2005/0080406 A1 | 4/2005 | Malecki et al. |
| 2005/0131401 A1 | 6/2005 | Malecki et al. |
| 2005/0131460 A1 | 6/2005 | Gifford, III et al. |
| 2005/0192626 A1 | 9/2005 | Widomski et al. |
| 2005/0192654 A1 | 9/2005 | Chanduszko et al. |
| 2005/0209636 A1 | 9/2005 | Widomski et al. |
| 2005/0216054 A1 | 9/2005 | Widomski et al. |
| 2006/0020275 A1 | 1/2006 | Goldfarb et al. |
| 2006/0027241 A1 | 2/2006 | Malecki et al. |
| 2006/0074410 A1 | 4/2006 | Malecki et al. |
| 2006/0241581 A1 | 10/2006 | Malecki et al. |
| 2006/0241582 A1 | 10/2006 | Malecki et al. |
| 2006/0241583 A1 | 10/2006 | Malecki et al. |
| 2006/0241584 A1 | 10/2006 | Malecki et al. |
| 2006/0247612 A1 | 11/2006 | Malecki et al. |
| 2006/0271030 A1 * | 11/2006 | Francis et al. .................. 606/27 |
| 2006/0271040 A1 | 11/2006 | Horne et al. |
| 2006/0271089 A1 | 11/2006 | Alejandro et al. |
| 2006/0276779 A1 | 12/2006 | Malecki et al. |
| 2006/0276846 A1 | 12/2006 | Malecki et al. |
| 2007/0010806 A1 | 1/2007 | Malecki et al. |
| 2007/0027445 A1 | 2/2007 | Gifford et al. |
| 2007/0038293 A1 | 2/2007 | St. Goar et al. |
| 2007/0044811 A1 | 3/2007 | Deem et al. |
| 2007/0078485 A1 | 4/2007 | Deem et al. |
| 2007/0088355 A9 | 4/2007 | Auth et al. |
| 2007/0093804 A1 | 4/2007 | Kaveckis et al. |
| 2007/0093805 A1 | 4/2007 | Auth et al. |
| 2007/0100324 A1 | 5/2007 | Tempel et al. |
| 2007/0100356 A1 | 5/2007 | Lucatero et al. |
| 2007/0106214 A1 | 5/2007 | Gray et al. |
| 2007/0112347 A1 | 5/2007 | Malecki et al. |
| 2007/0118155 A1 | 5/2007 | Goldfarb et al. |
| 2007/0123824 A1 | 5/2007 | Kaveckis |
| 2007/0123851 A1 | 5/2007 | Alejandro et al. |
| 2007/0123852 A1 | 5/2007 | Deem et al. |
| 2007/0129737 A1 * | 6/2007 | Goldfarb et al. .............. 606/151 |
| 2007/0203479 A1 | 8/2007 | Auth et al. |
| 2007/0287999 A1 | 12/2007 | Malecki et al. |
| 2007/0299434 A1 | 12/2007 | Malecki et al. |
| 2008/0004658 A1 | 1/2008 | Malecki et al. |
| 2008/0009859 A1 | 1/2008 | Auth et al. |
| 2008/0045937 A1 | 2/2008 | Whisenant et al. |
| 2008/0051703 A1 | 2/2008 | Thornton et al. |
| 2008/0051807 A1 | 2/2008 | St. Goar et al. |
| 2008/0058683 A1 | 3/2008 | Gifford et al. |
| 2008/0097489 A1 | 4/2008 | Goldfarb et al. |
| 2008/0140064 A1 | 6/2008 | Vegesna |
| 2008/0140068 A1 | 6/2008 | Taimisto |
| 2008/0140069 A1 | 6/2008 | Filloux et al. |
| 2008/0140070 A1 | 6/2008 | Filloux et al. |
| 2008/0140071 A1 | 6/2008 | Vegesna |
| 2008/0140074 A1 | 6/2008 | Horne et al. |
| 2008/0140112 A1 | 6/2008 | Horne |
| 2008/0140113 A1 | 6/2008 | Taimisto |
| 2008/0140170 A1 | 6/2008 | Filloux et al. |
| 2009/0069809 A1 | 3/2009 | Ootsubo |

* cited by examiner

BIOLOGICAL TISSUE CLOSING DEVICE

This application is based on and claims priority under 35 U.S.C. §119(e) with respect to U.S. Provisional Application No. 60/976,092 filed on Sep. 28, 2007 and U.S. Provisional Application No. 60/976,110 filed on Sep. 28, 2007, the entire content of both of which is incorporated herein by reference. This application is also based on and claims priority under 35 U.S.C. §119(a) with respect to Japanese Patent Application No. 2007-221898 filed Aug. 28, 2007 and Japanese Patent Application No. 2007-221908 filed Aug. 28, 2007, the entire content of both of which is hereby incorporated by reference.

TECHNOLOGICAL FIELD

The present invention generally relates to a biological tissue closing device which closes a defect occurring in a living body.

BACKGROUND DISCUSSION

Recently, patent foramen ovale (hereinafter referred to as PFO) has been identified as a cardiac factor in strokes and migraines. The PFO is a symptom in which the oval foramen (foramen ovale) for shortcircuiting blood between the left and right sides in the heart in the fetal period of a person's life remains even after the person has gown up. It is said that 20-30% of grown-up people have this disease.

The foramen ovale occurs at a septum secundum (Septum Secundum, hereinafter, referred to as atrial septum secundum) of the heart. The pressure on the left atrium side normally exceeds the pressure on the right atrium side in the heart and so the foramen ovale is occluded by a septum primum (Septum Primum, hereinafter, referred to as foramen ovale valve). However, when the pressure on the right atrium side exceeds the pressure on the left atrium side on a strain occasion (for example, when coughing, when holding on) or the like, the foramen ovale valve opens to the left atrium side and blood can flow from the right atrium side (venous side) into the left atrium side (arterial side). When a thrombus is included in this blood, the thrombus is shifted from the venous side to the arterial side, flows in a route of left atrium→left ventricle→aorta→brain, and can become a factor for a stroke, migrane or the like.

To treat such a disease, a treatment by a percutaneous catheter procedure is considered to be a desirable method if the same effect as an open heart surgery can be obtained.

A device performing a closing technique using the percutaneous catheter can be used in the case of closing defects such as a congenital atrial septal defect indwelled (ASD), a PFO, a ventricular septal defect (VSD) and a patent ductus arteriosus (PDA). A device used in the past is a device sandwiching the foramen ovale valve and the atrial septum secundum by using disk-shaped membranes or anchor members for closing the defect and these are indwelled in the body.

The membranes or anchor members are foreign substances for a human body and moreover, a thrombus can relatively easily be attached. In particular, when a thrombus attaches to a disk-shaped membrane or the like on the left atrium side, this flows and there is a possibility that it becomes a cause of a stroke, and there is also a fear that a foramen ovale valve of a thin wall thickness is broken. In addition, these members are not position-fixed in a state of being sandwiched and there is also a possibility of causing a positional displacement.

Consequently, recently, there has been proposed a PFO closing device described in International Application Publication No. WO2004/086944 A2 (Patent Document 1) (see summary, FIG. 10 and the like). This PFO closing device is a device in which an apparatus is inserted into the foramen ovale from the right atrium toward the left atrium, a foramen ovale valve is pulled to the foramen ovale so as to close it and the tissue is fused by applying electric energy. However, the foramen ovale, the foramen ovale valve and the atrial septum secundum are different not only in terms of sizes (small/large) but also in terms of thicknesses, shapes, etc. Depending on the individual and according to circumstances, the size or the like of the apparatus may be restricted a lot. Also, even on an occasion when the procedure is performed, there is a fear that it becomes difficult to pull various forms of foramen ovale valves to the foramen ovale at anytime and with reliability.

Consequently, as shown in Japanese Patent Application No. 2006-47636 (Patent Document 2) (see summary, FIG. 10 and the like), a PFO closing device proposed by the applicant here is constructed so that the foramen ovale valve and the atrial septum secundum are sandwiched by a pair of electrodes and the tissue is fused by applying electric energy from both the electrodes. This PFO closing device uses a clamper in which a stick portion and a sandwich member are composed of a pair of electrodes and with respect to one of them, the stick portion composed of a needle electrode is stuck into the foramen ovale valve. Thereafter, the foramen ovale valve and the atrial septum secundim are sandwiched with respect to the sandwich member which is the other electrode, the biological tissue is applied with electric energy, and the fusion is carried out. If this PFO closing device is used, foreign substances are not indwelled in the body, the construction becomes relatively simple, the procedure is comparatively easy and the foramen ovale valve and the atrial septum secundum can be fused with relative certainty.

However, this device is provided with a guiding catheter on the outside of a fine catheter, and the fine catheter is used by being stored in the guiding catheter. For the sake of attempting simplification of the operation, the stick portion which easily injures the blood vessel is provided position-fixedly at the distal tip of the fine catheter and there is employed a construction in which only the sandwich member moves with respect to the fine catheter, so that the sticking by the stick portion must be executed by moving the fine catheter in the guiding catheter and therefore, there is a drawback of insufficient degree of freedom for selecting the sticking position.

In particular, the sticking (puncture) operation is performed in a state in which the stick portion protrudes from the distal tip of the guiding catheter and by sticking the foramen ovale valve while moving the whole catheter forward and backward, so that the sticking position will be on an extension line of the catheter axial line (axis) and it is possible to execute the sticking or puncture at a desired position by using a positioning member, but when moving the sticking portion, there is a fear that a mis-sticking into the front side of the foramen ovale valve will occur caused by a body movement which happens in the case of a shallow level of anesthesia. It is preferable or perhaps ideal to select the sticking position to be right under the position at which the foramen ovale valve and the atrial septum secundum overlap, but it is extremely difficult to adjust by hand the position of the needle member of the stick portion, which is positioned at the distal tip of the fine long catheter.

SUMMARY

The biological tissue closing device here includes a stick portion and sandwich member that are movable independently with respect to the catheter to help heighten the degree of freedom for selecting the sticking position so that a desired sticking position can be selected.

The biological tissue closing device includes a clamper including a stick portion provided at a distal portion of a catheter for sticking a biological tissue, and a sandwich member for sandwiching the biological tissue in cooperation with the stick portion. An electric energy supply unit supplies electric energy to the clamper, and the biological tissue is fused by making the stick portion and the sandwich member of the clamper electrode members, by sandwiching the biological tissue with the clamper and by supplying electric energy from the electric energy supply unit, wherein the clamper makes each of the stick portion and the sandwich member movable independently with respect to the catheter.

By making a stick portion and a sandwich member of a clamper movable independently with respect to a catheter respectively in the biological tissue closing device, it is possible, with respect to the stick portion, to select and stick an arbitrary position, for example, such an ideal sticking position as a directly-close position of a position at which a foramen ovale valve and an atrial septum secundum which are biological tissues are overlapped and thus, it is possible to attempt the improvement in smoothness, safety and also certainty of the procedure.

Retracting the stick portion from the distal region of the catheter in a tilting manner with respect to the axis of the catheter, it is possible to protrude the stick portion toward the side direction of the catheter and when the catheter is moved in the axial direction and comes to a predetermined position, it is possible to execute the stick and it is possible to execute the stick at an ideal sticking position easily.

The stick portion preferably includes a needle member provided at a distal portion of the catheter, wherein the needle member is elastically deformed by a holder including a lumen receiving the needle member and depending on the lumen shape, protrusion in the side direction of the needle member becomes possible.

The distal side of the stick portion preferably includes a plurality of needle members which are mutually expandable and shrinkable towards and away from one another. The stick needle is able to contact the foramen ovale valve over a relatively wide region by the plurality of the needle members and it is possible to sandwich the foramen ovale valve and the atrial septum secundum after the sticking over the wide region and the fusion region of the biological tissue becomes wider.

A holder can be provided at a distal portion of the catheter and includes a plurality of lumens in which the needle members are positioned. The shapes of the lumens expand mutually toward the distal direction and the needle members are moved forward and backward along the lumen shapes.

The plurality of needle members can be configured to possess shapes expanding mutually toward the distal direction, and the needle members in a state in which expansion is closed elastically are made to be housable with respect to a holder provided at a distal portion of the catheter, wherein the housing includes a lumen into which the stick portion is inserted. The distal side of the stick portion can be diverged or converged depending on the elastic force by protruding and pulling back the needle member along the lumen.

The distal portion of the stick portion is branched into a plurality of portions and the branch portions expanded mutually toward the distal direction constitute the needle members. The needle members in a state in which the branch is closed (contracted) are made to be housable with respect to a holder provided at a distal portion of the catheter and including a lumen into which the stick portion is inserted.

The stick portion can be made of a shape memory material, and the plurality of needle members expand by a shape-recovery temperature higher than the temperature of the environment of use. It is thus possible to expand/shrink the distal side of the stick portion by changing the temperature of the stick portion.

The stick portion can be made of a shape memory material whose distal tip is branched into a plurality of portions, with the branch portions expanding mutually toward the distal direction to constitute the needle members. The needle members can be held in a state in which the branch is closed at the temperature of the environment of use, and the needle members expand by a shape-recovery temperature higher than the temperature of the environment of use and so it is possible to expand/shrink the distal side of the stick portion provided in a manner of being branched into the plurality of portions by changing the temperature of the stick portion.

Heating the stick portion made by the shape memory material to the shape-recovery temperature can be performed by supplying electric energy from the electric energy supply unit to the stick portion.

The needle member can be deformed before the clamping in a direction away from the sandwich member, for example by possessing a curved arc shape or being formed in a shape such as <.

The distal portion of a guiding catheter for guiding the catheter can be bent. Regardless of a state of the foramen ovale valve and the atrial septum secundum which differ depending on the person, it is easier for the catheter to be directed to the foramen oval (opening portion formed at biological tissue) between the foramen ovale valve and the atrial septum secundum easier than a case of a straight shape, and safety, convenience and speediness of the procedure are improved.

The biological tissue closing device is preferably provided at the proximal portion of the catheter with an operation unit for operating the clamper. The operation unit and the clamper are coupled by an operation member inserted into the catheter, and it is possible to operate the clamper only by the operation unit at hand without moving the whole catheter forward and backward. It is also possible to execute the operation of the sticking and the sandwiching more easily and also accurately and it is possible to execute also the sticking or sandwiching operation by a so-called single hand operation, and the operability is improved more.

BRIEF DESCRIPTION OF THE DRAWINGS

FIGS. 17(A) and (B) are perspective views of another example of a positioning hold mechanism, in which FIG. 17A shows a state before deformation and FIG. 17B shows a state after deformation.

DETAILED DESCRIPTION

FIGS. 1-6 illustrate aspects of a PFO closing device according to a first exemplified embodiment disclosed herein. It should be noted in FIG. 2 that the operation unit 70 is described as a state of being demagnified because of space limitations.

First, generally speaking, the PFO closing device disclosed here includes a clamper K for sandwiching a foramen ovale valve M2 and an atrial septum secundum M1; and an energy supply unit 20 for supplying energy by which a biological tissue M (general term referring to M1, M2) of a portion sandwiched by the clamper K is welded or fused together, wherein the clamper K is positioned in a percutaneous catheter 30 from a distal tip thereof so as to be forward-movable to protrude distally beyond the distal end of the catheter and backward-movable.

This device, when used, is first inserted, for example, from a femoral vein J in a state in which there is housed in a guiding catheter 31 the entire clamper K which is provided at the distal tip of the catheter 30. When the distal tip reaches the region of the heart at which the procedure is executed, the clamper K is moved to protrude from the distal tip of the guiding catheter 31, and the tissue of the atrial septum secundum M1 and the foramen ovale valve M2 of the heart having the defect O of the foramen ovale are sandwiched by the clamper K. In this sandwiched state, the clamper K is supplied with electric energy, the tissue of the atrial septum secundum M1 and the foramen ovale valve M are welded and fused, and the defect O is closed. It should be noted in FIG. 1 that L denotes a left atrium and R denotes a right atrium.

Figure 1:
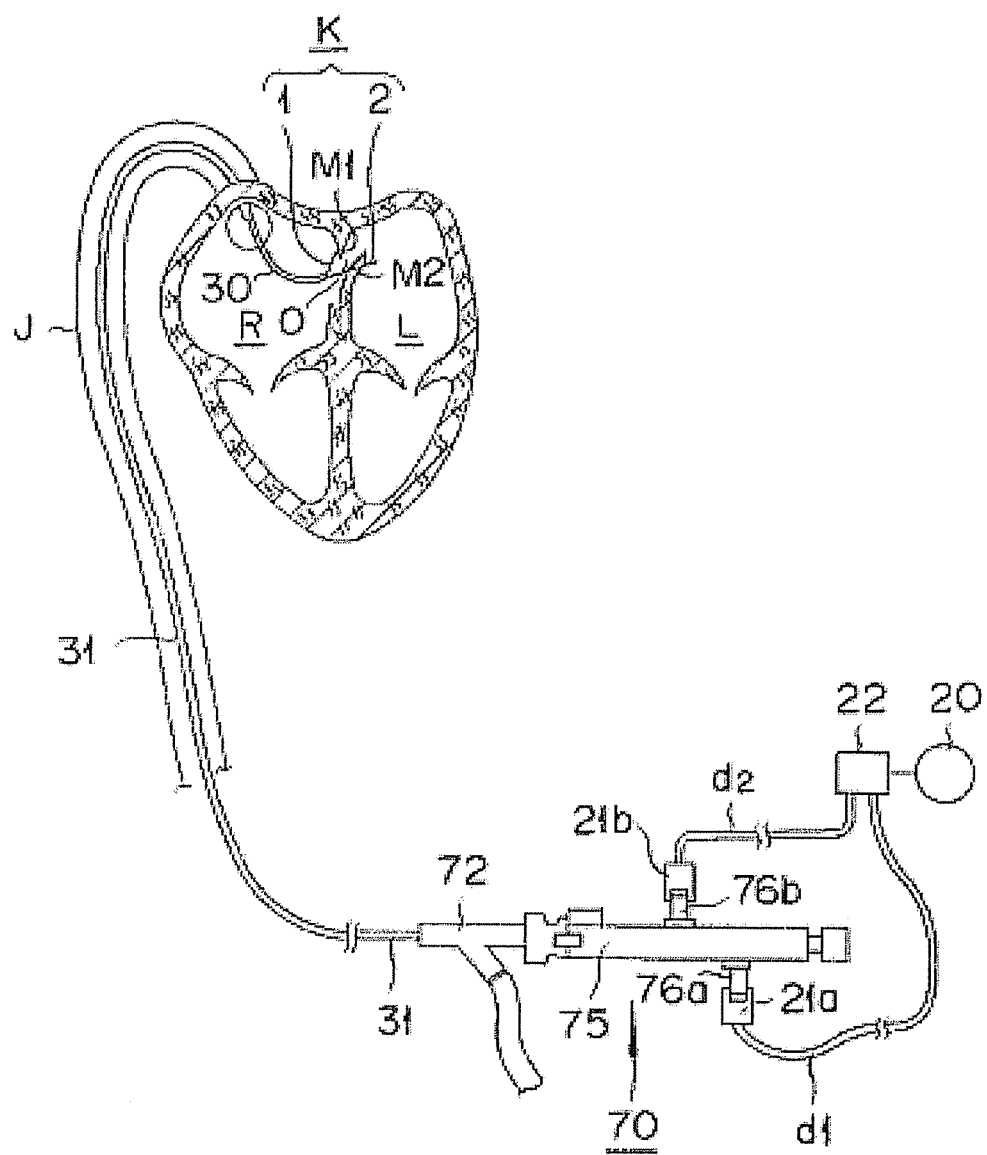
FIG. 1 is a schematic cross-sectional view of a PFO closing device according to a first exemplified embodiment disclosed here.
Figure 2:
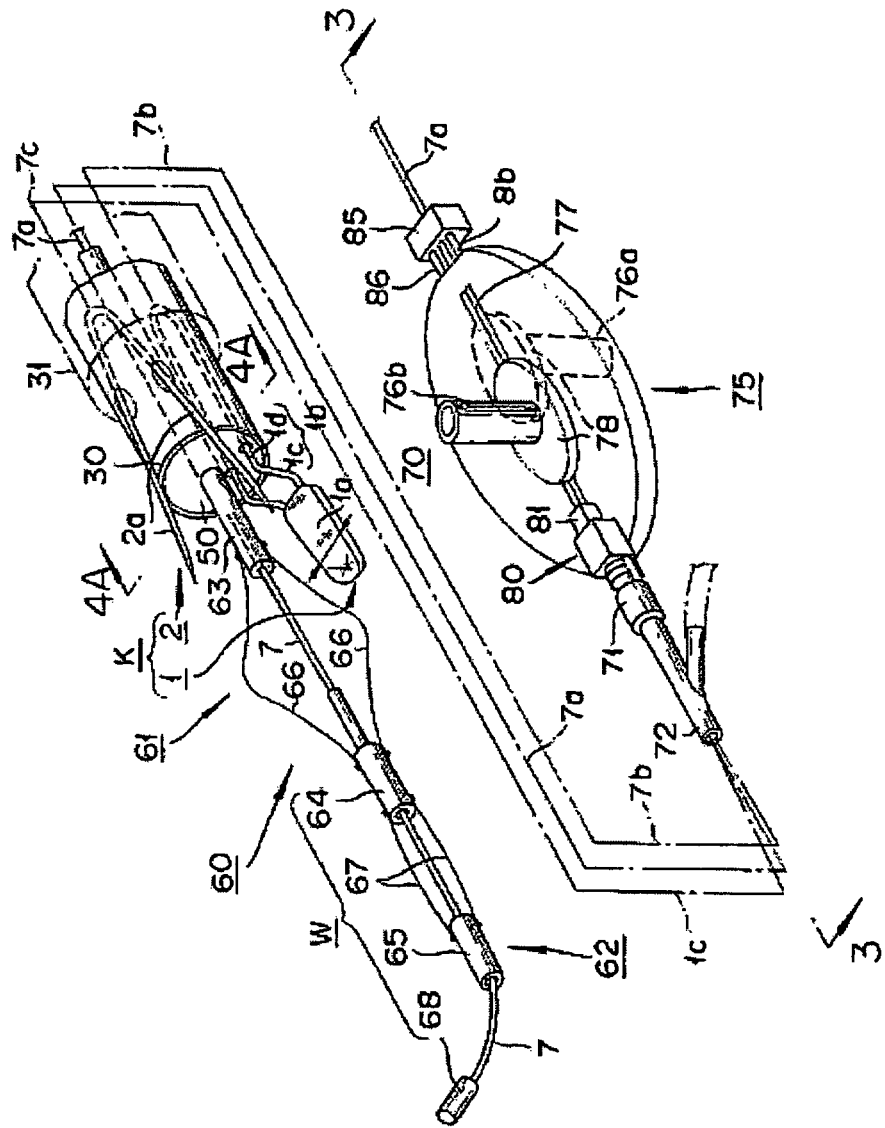
FIG. 2 is a perspective view of a main portion of the closing device shown in FIG. 1.

This device, as shown in FIGS. 1 and 2, also includes a preferably hand operated operation unit 70 provided on the proximal side for operation by the physician or other user; a guiding catheter 31 mounted on the operation unit 70 for the proximal tip thereof; the catheter 30 provided in the guiding catheter 31, the clamper K provided at a distal portion of the catheter 30; and a positioning hold mechanism 60 for executing the clamper k procedure stably and accurately. It should be noted in the following explanation that the operation unit 70 side of the device is referred to as the proximal side and the clamper K side or the foramen ovale valve M2 side is referred to as the distal side.

As shown in FIG. 2, the clamper K of this exemplary embodiment comprises a sandwich member 1 directly contacting one side surface of the atrial septum secundum M1, and a stick portion 2 adapted to be stuck into or puncture the foramen ovale valve M2. The sandwich member 1 and the stick portion 2 function as electrode members respectively. The proximal portions of the sandwich member 1 and the stick portion 2 are held by a holder 50 provided at the distal tip of the catheter 30 and are constructed to be moved relative to the holder to protrude distally from the distal end of the holder 50.

The sandwich member 1 is comprised of a main body portion 1a including generally a flat plate shape and a predetermined width L, and a pair of wire portions 1b connected to the proximal portion of the main body portion. One piece of an operation member 7b is connected to the proximal side of the wire portion 1b. By moving the operation member 7b forward and backward in the axial direction, the sandwich member is displaced to protrude from the distal tip of the catheter 30 or to approach toward the stick portion 2 side.

Each wire portion 1b includes a bend portion 1c and a straight-shaped portion 1d, with the straight-shaped portion 1d being positioned in a respective lumen L3, L4 (see FIG. 4) of the holder 50. The straight-shaped portion 1d is positioned in the respective lumen L3, L4 to be movable forward and backward, so that if the operation member 7a is traction-operated or pulled rearwardly, when the bend portion 1c moves into the entrance portion of the respective lumen L3, L4 of the holder 50, the sandwich member 1 is displaced to approach and move away from (separate with respect to) the stick portion 2. It is thus possible to carry out the sandwiching of the biological tissue by both the electrode members comparatively easily and smoothly even in case of the distal portion of the fine catheter 30.

Also, it is possible for the wire portion 1b and the operation member 7b to be constructed of one piece of wire. A SUS material may be used as a material for fabricating the main body portion 1a. It is preferable to use a material which does not exert bad influence to a living body such as, for example, gold, silver, platinum, tungsten, palladium or alloys of these, Ni—Ti alloy, titanium alloy and the like.

The stick portion 2 is held by lumens L1, L2 formed in the holder 50 so as to be movable forward and backward. The distal portion of the stick portion is constructed to be retractable from the holder 50 by operating an operation member 7c connected to the proximal side of the stick portion 2. More specifically, each of the stick portion 2 and the sandwich member 1 of the clamper K is configured to be movable independently in the axial direction with respect to the catheter 30. However, the stick portion 2, differently from the sandwich member 1, is retractable from the holder 50 and can be configured to protrude freely at a desired position. Also, it is possible for the wire portion 1*b* and the operation member 7*b* to be constituted by one piece of wire.

By making each of the stick portion 2 and the sandwich member 1 of the clamper K movable independently with respect to the catheter 30 by using the operation members 7*b*, 7*c* in this manner, it is possible to stick the stick portion 2 at an arbitrary position, so that it is possible to execute the procedure relatively smoothly, safely and also certainly.

In this illustrated embodiment, the stick portion 2 of the present exemplified embodiment is comprised of two pieces in the form of needle members 2*a*, 2*a*. As shown in FIG. 4B, the stick portion 2 is preferably formed such that the two needle members 2*a*, 2*a* expand in a mutually widening manner, that is so that the two needle members diverge away from one another in the distal direction. With this distally widening configuration or shape, the stick portion 2 is able to stick or puncture the foramen ovale valve M2 over a wider region and the sandwich region with respect to the sandwich member 1 is expanded.

Also, it is possible for both the needle members 2*a*, 2*a* to be constructed to move in/out from the distal region of the catheter 30 in a tilting manner with respect to the axial center line (axis) of the catheter 30, in other words such that both the needle members 2*a*, 2*a* will move in/out from the side direction of the catheter 30. To explain it with reference to, for example, FIG. 8, it is ideal for the sticking position to be a foramen ovale valve portion in close vicinity of the position at which the foramen ovale valve M2 and the atrial septum secundum M1 overlap each other (T portion shown by alternate long dashed short dashed line), so that if it is approached to such a sticking position, it becomes possible to execute the sticking by aiming at this.

The closing device also includes a positioning hold mechanism 60 (described in detail later) provided with a main tube 63 inserted into or positioned in a large lumen L5 at the center of the holder 50 and a main operation rod 7*a*. Before using the sandwich mechanism K, the stick portion 2 is positioning-held by using the positioning hold mechanism 60 and in this case, the sticking or puncturing is executed in a state in which the main operation rod 7*a* is inserted into the foramen ovale O beforehand. In other words, the stick portion 2 is configured to be stuck into (puncture) the foramen ovale valve portion by passing through a passway which is restricted a certain degree by the main operation rod 7*a*.

If the stick portion 2 is operated in such a state, there is a concern that the sticking or puncturing can be carried out only for the front side of catheter 30, but with the needle members 2*a*, 2*a* protruding in angled manner (e.g., upward direction in FIGS. 4(A) and 4(C)) as disclosed and illustrated here (protruding in a manner such that the needle members 2*a*, 2*a* are not parallel to the axis of the holder 50), the stick portion is naturally directed toward a closed position of the ideal overlapping position T as the distal tip of the catheter 30 approaches the foramen ovale O. Moreover, it is possible for the stick portion 2 to execute the sticking action more independently, so that it is possible to choose the most preferable sticking position and the sticking becomes possible at that position.

To effect movement of the stick portion in an angled direction (e.g., up and down direction), as shown in FIG. 4A-FIG. 4C, the lumens L1, L2 in the holder 50, in which are positioned the elongated needle members 2*a*, 2*a* forming the stick portion, are oriented to tilt at least upward in the distal direction. Thus, each of the lumens L1, L2 in the holder 50 is angled upwardly away from the central axis of the catheter in the distal direction. The needle members 2*a*, 2*a* are guided by the lumens L1, L2 to protrude in the illustrated manner so that the two elongated needle members 2*a*, 2*a* diverge away from the sandwich member 1 as shown in FIG. 4(C) in the distal direction. It is possible for the angle of inclination θ of this tilt portion to be set to any value, but generally, around 10° to 30° is preferable and according to circumstances, it is also possible to set it around 90°.

Also, according to circumstances, it is also possible for both the needle members 2*a*, 2*a* themselves to possess curved arc shapes in which they curve in a direction away from the sandwich member 1 or to be bent in a < shape. With needle members that are curved or bent, it is easier to further protrude both the needle members 2*a*, 2*a* to the side direction by simply moving both the needle members 2*a* in the axial direction of the catheter 30.

Figure 5:
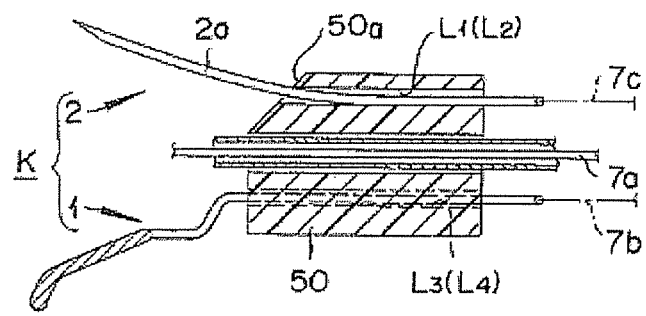
FIG. 5 is a cross-sectional view similar to FIG. 4C illustrating a modified example of a holder of the closing device.
Figure 6:
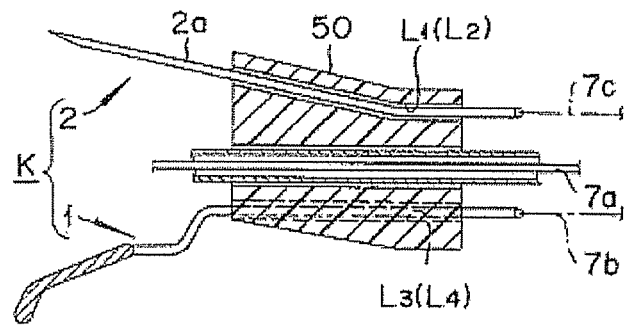
FIG. 6 is a cross-sectional view similar to FIG. 4C illustrating another modified example of the holder.

It is also possible to change not only the shapes of both the needle members 2*a*, 2*a* themselves, but also the shape of the holder 50 and the arrangement which holds the needle members 2*a*, 2*a*. For example, as shown in FIG. 5, a cut-out portion 50*a* is formed at the distal tip of the holder 50 so that the upper portion of the holder 50 at which the lumens L1, 12 open is inclined. It is possible to use the lumens L1, L2 to move both the needle members 2*a*, 2*a* more easily in the side direction. As shown in FIG. 6, the holder 50 itself is deformed and it is possible for the needle members 2*a*, 2*a* to be tilted so as to move more easily in the side direction.

As shown in FIG. 2, the stick portion 2 of the present exemplified embodiment is constructed to include two fine elongated pieces each forming one of the elongated needle members 2*a*, 2*a*. The needle members 2*a*, 2*a* possess circular cross-sections perpendicular to their axes and possess sharply pointed front ends. The needle members 2*a*, 2*a* are arranged so as to mutually expand (diverge away from one another in the distal direction). If the foramen ovale valve M2 is stuck into by such a stick portion 2, the region covered by the two pieces of needle members 2*a*, 2*a* is relatively wide, and it is possible, even for various forms of the foramen ovale valve and the atrial septum secundum, to execute positioning of at least one electrode member to the foramen ovale valve M2, and the sandwiching operation of the biological tissue M becomes relatively easy. It is also possible for the needle members 2*a*, 2*a* to possess cross-sectional shapes perpendicular to the axes that are other polygonal shapes.

Solid cylindrical members are not always necessary for the needle members 2*a*, 2*a*, and it is possible to employ hollow cylindrical shaped members. It is preferable for the outer diameter of the needle members 2*a*, 2*a* to be around 0.1 mm to 2 mm in order to be installed in the catheter 30. The material forming the needle members 2*a*, 2*a* is preferably a SUS material, though it is also possible to use a material which does not exert bad influence to a living body such as, for example, gold, silver, platinum, tungsten, palladium, titanium or alloys of these and the like.

Though not limited, it is preferable for the mutual distance of the two pieces forming the electrode portions 3*a*, 3*a* to be selected such that the foramen ovale valve M2 and the atrial septum secundum M1 can be sandwiched in a certain range. Also, with respect to the number of pieces forming the electrode pieces, it need not be only two pieces as a larger number of pieces can be employed.

The operation members 7*b*, 7*c* for moving the sandwich member 1 and the stick portion 2 in/out from the catheter 30 can be any kind of members, though preferably fine wire-shaped members, so long as they can move the clamper K forward and backward in the catheter 30 and permit the flow of electric current therethrough. It is preferable to use a wire such as, for example, stainless, Ni—Ti, titanium and the like for the operation members 7*a*, 7*b*. Both the operation members 7b, 7c are positioned in the catheter 30 and are connected with the energy supply unit 20 through operation levers 76a, 76b, connection members 21a, 21b, conductive wires d1, d2 and a control unit 22 which will be described later.

Figure 3:
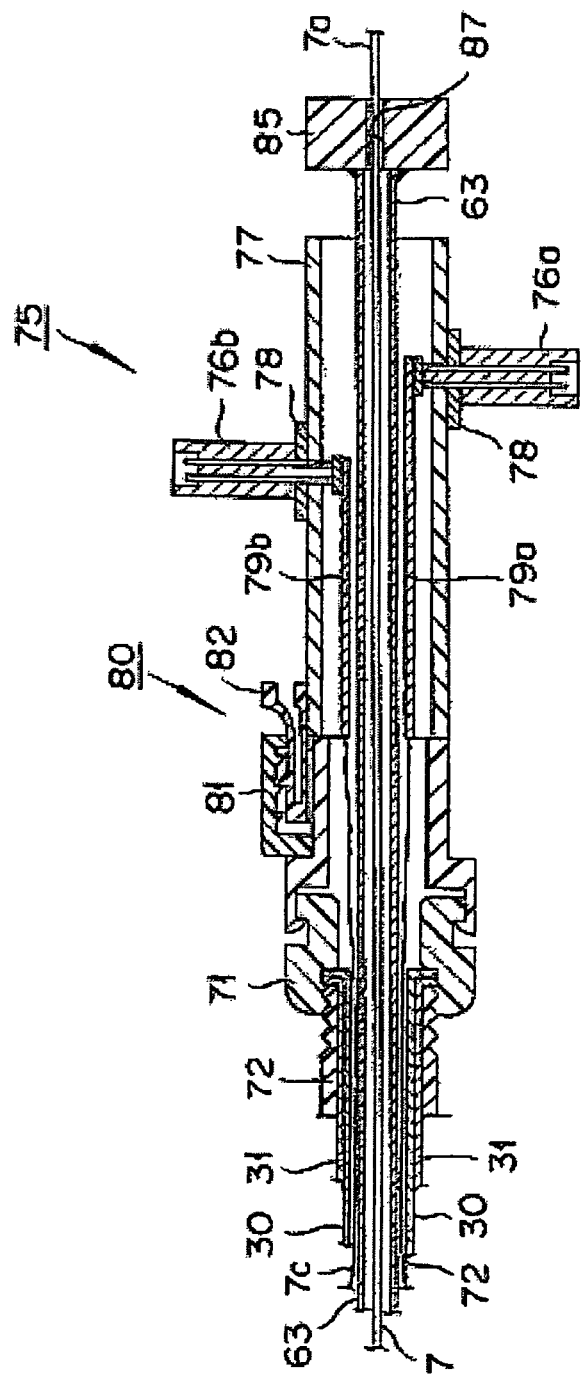
FIG. 3 is a cross-sectional view of the closing device taken along the section line 3-3 in FIG. 2.

The holder 50 includes, as shown in FIG. 4A, a plurality of lumens L1-L5. However, it is also possible that these lumens L1-L5 can be constituted by catheters respectively. As shown in FIG. 1 to FIG. 3, the operation unit 70 includes a handle member 75 composed of a flat member such that the surgery operator can grasp it with a single hand. The operation lever 76b protrudes upwardly from the surface side (upper surface side) of the handle member 75. The operation lever 76b is coupled to the proximal side of the operation member 7c of the stick portion 2. Another operation lever 76a protrudes downwardly, in the direction opposite the operation lever 76b, from the rear surface side (lower surface side) of the handle member 75. The operation lever 76a operates the operation member 7b of the sandwich member 1.

The operation levers 76a, 76b are slidably positioned in a slide groove 77 formed on the handle member 75, and each is provided with an enlarged brim portion 78 at the one end portion that is configured to relatively smoothly slide without falling out of the groove.

The operation members 7b, 7c are wired to the end portions of the operation levers 76a, 76b. Connection members 21a, 21b composed of sockets, couplers or the like are connected to the distal tips of the conductive wires d1, d2 which are electrically connected to the electric energy supply unit 20. The connection members 21a, 21b and the upper end portions of the respective operation levers 76a, 76b are configured to detachably engage one another, for example by way of a concave-convex-fit. Owing to this fit, the electric energy supply unit 20 and the operation levers 76a, 76b are in an electrically conductive state.

Consequently, after the procedure concerning the sticking and the sandwich caused by both the operation levers 76a, 76b is completed, if the connection members 21a, 21b are connected to the respective operation levers 76a, 76b, it is possible to supply electric energy by which the foramen ovale valve M2 and the atrial septum secundum M1 are fused together or joined. In other words, not only is it possible to supply electric energy at a desired point in time but it is also possible to execute the procedure comparatively accurately and also smoothly in case of executing the procedure without concern that the conductive wires d1, d2 will become obstructed.

It is possible to directly connect the respective operation members 7b, 7c with the respective operation levers 76a, 76b by brazing or the like. However, in the present exemplified embodiment, slide pieces 79a, 79b face the slide groove 77 formed on the handle member 75, and the proximal sides of the respective operation members 7b, 7c are brazed on the distal tips of the slide pieces 79a, 79b and the inner ends of the respective operation levers 76a, 76b are brazed on the proximal tips of the slide pieces 79a, 79b. With this construction, the operability of the device, as well as the strength or durability, is improved. The slide pieces 79a, 79b are provided slidably in the groove formed on the handle member 75.

In addition, the operation unit 70 of the present exemplified embodiment also includes a lock mechanism 80 for locking a state in which the stick portion 2 protrudes from the distal portion of the catheter 30 at the distal portion of the handle member 75.

The lock mechanism 80 comprises a bump member for restricting the sliding movement of the operation lever 76b for the needle members on the distal side of the slide groove 77 formed on the handle member 75 and the sliding movement is locked by pressing the operation lever 76b for the needle members to the bump member. If the stick portion 2 is locked in a state in which it protrudes from the distal portion of the catheter 30, it is possible to supply electric energy while maintaining the protruding state of the stick portion 2, and so it is possible to avoid the stick portion 2 being deviated at the time of supplying electric energy so that the procedure can be carried out more stably and also accurately.

It is also possible for the lock mechanism 80 to employ any form of mechanism that makes it possible to lock the operation lever 76b for the needle. But as shown in FIG. 3, if a tubular block 81 is fixed on the handle member 75 and a slide member 82 is movably positioned in the tubular block 81, it is possible to adjust the fixed position of the operation lever 76b for the needle.

The energy supply unit 20 is a unit for supplying electric energy to the clamper K and a well-known system construction can be employed. Thus a detailed description is not set forth here. But if easiness of control is taken into account, it is preferable to employ an electrical power supply regardless of whether it is a direct-current power supply or an alternate-current power supply. However, it is also possible to employ not only this kind but also any kind of supply unit if it can supply energy in which the foramen ovale valve M2 and the atrial septum secundum M1 which are sandwiched by the clamper K are melted, fused or joined by the heat and are pressed and fixed by an adhesive agent such as collagen, erastin and the like. For example, it is also possible to use a super sonic wave, laser, microwave or high frequency and the like.

Also, it is possible for an electric energy supply system to be a monopolar system which energizes between the stick portion 2 or the sandwich member 1 of the right atrium R side and a counterpart pole plate (counterpart electrode) at a backbone portion, a bipolar system which energizes between the sandwich member 1 of the right atrium R side and the stick portion 2 of the left atrium L side, and the like. In particular, if the energy supply system is formed as a bipolar system for controlling the current by the impedance of the biological tissue between the stick portion 2 and the sandwich member 1, there are advantages in that it can have correspondence relatively easily in response to the state of the tissues of the foramen ovale valve M2 and the atrial septum secundum M1 which differ depending on the individual, and the safety and the convenience of the procedure can be enhanced.

Figure 4:
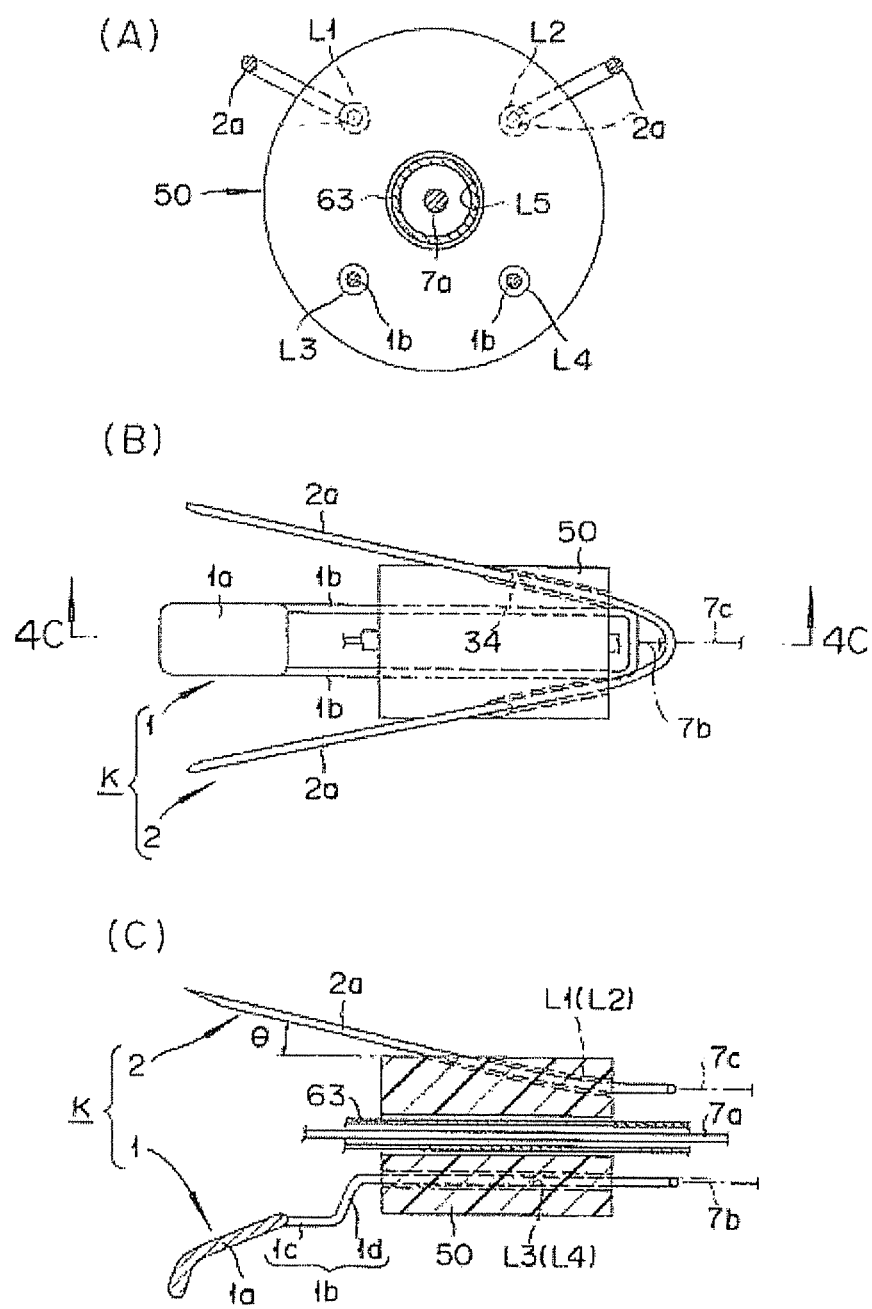
FIG. 4A is a cross-sectional view of the closing device taken along the section line 4A-4A line in FIG. 2.
FIG. 4B is a plan view of the portion of the device shown in FIG. 4A.
FIG. 4C is a cross-sectional view of the device taken along the section line 4C-4C in FIG. 4B.

Five lumens L1-L5 are established in the holder 50 as shown in FIG. 4, and the stick portion 2 and the sandwich member 1 are positioned in the first and second lumens L1, L2 and the third and fourth lumens L3, L4 as mentioned above, and the positioning hold mechanism 60 is provided in the fifth lumen L5 having the maximum aperture size and positioned at the center of all the lumens.

The positioning hold mechanism 60, as shown in FIG. 2, generally includes a positioning portion 61 for positioning the stick portion 2 with respect to a foramen ovale O and a holding portion 62 for holding the foramen ovale valve M2 with respect to the sticking direction of the stick portion 2 so as not to readily allow backward movement of the foramen ovale valve M2, and normally it is housed in the guiding catheter 31, but is pushed out from the guiding catheter 31 by the main operation rod 7a and the main tube 63 during use.

To describe it in more detail, there are provided in the center lumen L5 a main tube 63 provided for pulling and withdrawing the positioning hold mechanism 60 in/from the catheter and for purpose of aiming at reinforcement of the catheter 30, and an main operation rod 7a which is provided so as to move forward and backward freely in the axial direction in the main tube 63.

There is provided at the distal portion of the main tube 63, as the positioning hold mechanism 60, a positioning portion 61 which is operated so as to expand or shrink by the operation of the main operation rod 7a and constituted by a pair of a first elastic wires 66 (first elastic member) coupling the main tube 63 and a middle sleeve body 64; and a hold portion 62 which includes a contact member 68 at the distal portion of the main operation rod 7a, a distal tip sleeve body 65 and a pair of a second elastic wires 67 (second elastic member) coupling the middle sleeve body 64 and the distal tip sleeve body 65. The foramen ovale valve M2 is held by the contact member 68 and the distal tip sleeve body 65.

With respect to the positioning portion 61, the main operation rod 7a protrudes from the distal tip of the main tube 63, the first elastic members 66 are displaced outward in a radial direction by the operation and movement of the main operation rod 7a (backward in the axial direction), the first elastic members 66 press the inner fringe of the foramen ovale O with approximately equal elastic forces, and the stick portion 2 is center-aligned with respect to the foramen ovale O. In other words, the positioning portion 61 positions the stick portion 2, located between the two first elastic members, at the center portion of the foramen ovale O.

The holding portion 62 includes a bending mechanism W for bending the distal portion of the main operation rod 7a by operating the main operation rod 7a in the axial direction so as to move (backward movement). The bending mechanism W bends the holding portion 62 to face in the direction in which the stick portion 2 sticks the foramen ovale valve M2 and operates to hold the foramen ovale valve M2. Here, the bending mechanism W is comprised of the middle sleeve body 64, the distal tip sleeve body 65, the second elastic wire(s) 67 for coupling both the sleeve bodies 64, 65, and the contact member 68.

The proximal tip of the first elastic wire(s) 66 is welded on the distal tip of the main tube 63 and the distal side of the first elastic wire(s) 66 is welded on the middle sleeve body 64. On the other hand, the proximal tip of the second elastic wire(s) 67 is welded on the distal tip of the middle sleeve body 64 and the distal side of the second elastic wire(s) 67 is welded on the distal tip sleeve body 65.

It is preferable, as a specific example of the first and second elastic wires 66, 67, to use a metallic wire such as stainless steel, nickel-titanium, super elastic alloy (for example, Ni—Ti alloy) and the like with an outer diameter of around 0.1 mm to 0.5 mm. It is also possible to prevent the tissue from being wounded by coating a metallic wire with a (soft) resin tube.

The holding portion 62 has a construction in which the first elastic wire(s) 66 on the proximal side bends prior to the second elastic wire(s) 67 on the distal side, the positioning of the stick portion 2 is executed, subsequently the main operation rod 7a itself is deformed (bent) accompanied by the contact member 68 and the distal tip sleeve body 65, and the positioning portion 61 holds the foramen ovale valve M2 after positioning the stick portion 2.

It is also possible to use a second elastic wire(s) 67 having higher stiffness materially than that of the first elastic wire 66, or to use an easily-deformable portion formed by bending a portion of the first elastic wire 66 beforehand or the like and when a traction (backward) force is applied, the first elastic wire 66 is bent previously compared with the second elastic wire 67 by the deformation of the easily-deformable portion.

The first elastic wire 66 of the proximal side engages the inner fringe of the foramen ovale O simply by the backward traction or pulling of the main operation rod 7a and so the positioning of the stick portion 2 can be executed. Upon applying further traction or backward pulling, the second elastic wire(s) 67 of the distal side deforms like an arc shape outward in the radial direction, and it is possible to hold the foramen ovale valve M2 so as not to allow the backward movement of the foramen ovale valve M2 such that it becomes easier for the stick portion 2 to be stuck or to penetrate the foramen ovale valve M2.

Also, the main operation rod 7a is configured to be 360° rotatable centering around the axis of the main tube 36. With the main operation rod 7a being 360° rotatable, when the distal tip of the main operation rod 7a is inserted to the vicinity of the foramen ovale O, it is possible to position-change the main operation rod 7a rotatingly and even if a state of the foramen ovale O is deformed variously, it is possible, regardless of the shape state of the foramen ovale O, to insert the distal tip of the device into the foramen ovale O and it is possible not only to simplify the procedure but also to execute it speedily.

The rear end portion of the handle member 75 is provided with a handle member 85 (handle member for main tube) which is used to move the main tube 63 forward and backward through two slide rails 86. The proximal side of the main tube 63 is firmly fixed at the handle member 85 so that when the handle member 85 is pulled toward the direction moving away from the handle member 75 (i.e., when it is pulled backward), it is possible to pull the main tube 63 into the center lumen L5 of the catheter 30. In association with this, the whole positioning hold mechanism 60 is drawn into the catheter 30.

It should be noted that in order to configure the main operation rod 7a to be 360° rotatable, the main operation rod 7a is inserted into a through-hole 87 of the handle member 85 and is extended.

The material constituting the main tube 63 can be a deformable elastic material such as, for example, polyimide resin, polyurethane, PET, nylon, fluorine resin, polypropylene and the like.

Also, it is also possible for the main operation rod 7a to employ any kind of rod if it is a fine hollow cylindrical wire and possesses a comparison suitability, but it is preferable to use a fine tube such as, for example, stainless, Ni—Ti, titanium and the like.

A Y connector 72, into which a contrast medium or the like can be injected, is coupled to the distal tip of the handle member 75 through a coupling member 71, and the proximal tip of the catheter 30 and the end portion of the guiding catheter 31 are held at the coupling member 71.

The distal tip of the guiding catheter 31 in this exemplified embodiment is bent gently in an arc shape in order to make it easier to be inserted into the foramen ovale O between the foramen ovale valve M2 and the atrial septum secundum M1. The foramen ovale valve M2 and the atrial septum secundim M1 differ depending on the individual, so that when the distal tip of the guiding catheter 31 is bent, the guiding catheter 31 itself is rotatingly moved and it is possible to insert the guiding catheter 31 into the foramen ovale O at a position in which the insertion becomes easiest, and safety and convenience of the procedure are improved compared with the case of a straight shape.

The operation of this embodiment is as follows with reference to FIGS. 7-10. In FIGS. 10A-10D, the shapes and positions of the second elastic wire 66 are illustrated relative to the sandwich member 1 and the stick portion 2. In order to facilitate an understanding, they are shown in positions displaced by 90° and are different from the actual deformation states and positions.

First, the surgery operator moves the handle member 85 of the operation unit 70 backward with respect to the handle member 75 to reach a state in which the sandwich member 1, the electrode portions 3a, 3a and the like are housed or positioned in the guiding catheter 31. In this state, the distal tip of the guiding catheter 31 is inserted from a predetermined position of the living body by using a guide wire as a guide thereof until it reaches the right atrium R by passing through the femoral vena cave J. Here, it is also possible to insert only the guiding catheter 31 into the living body and afterward to insert the catheter 30 by using that guiding catheter 31 as a guide.

Figure 7:
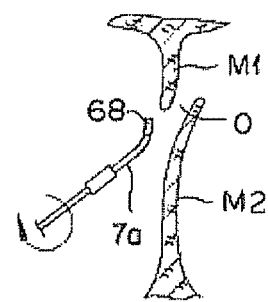
FIG. 7 is a cross-sectional schematic illustration of the main operation rod during insertion into a foramen ovale.

When the distal tip of the guiding catheter 31 reaches the right atrium R, as shown in FIG. 7, the catheter 30 is pushed out and moved toward the foramen ovale O between the foramen ovale valve M2 and the atrial septum secundum M1. The distal tip of the guiding catheter 31 is curved, so that it is possible to move it toward the foramen ovale O comparatively easily.

Next, the main operation rod 7a is moved forward and, as shown in FIG. 10A, the distal tip of the main operation rod 7a distally protrudes beyond the distal tip sleeve body 65 and is inserted into the left atrium L. It is possible to visually observe this protruding state from the outside if a marker is provided on the contact member 68 or the like. It is also possible to identify in a tactile manner the position of the distal tip of the main operation rod 7a when the distal tip of the main operation rod 7a bumps an inner wall of the left atrium L as a result of this protrusion even in a case in which it is difficult to visually observe. In the present exemplified embodiment, the main operation rod 7a is rotatable by 360° so that, as shown in FIG. 7, when the main operation rod 7a is moved forward while rotating, it is possible to insert it into the foramen ovale O more easily.

After identifying the location of the distal position of the main operation rod 7a, as shown in FIG. 10B, the main operation rod 7a is moved backward until the contact member 68 of the main operation rod 7a engages or contacts the distal tip sleeve body 65 (amount of backward movement is δ1 in FIG. 10B). Then, the handle member 75 is operated, and the second elastic member 67 (second elastic wires), the sandwich member 1 and the stick portion 2 are positioned in the vicinity of the foramen ovale valve M2 and the entire holding portion 62 is inserted into the left atrium L side.

When the main operation rod 7a is further moved backward (amount of backward movement is δ2 in FIG. 10C), the operation force for the backward movement is transmitted by the main operation rod 7a to the first elastic member 66 (first elastic wires) firmly fixed on the distal tip of the main tube 63 through the contact member 68, the distal tip sleeve body 65, the second elastic wires 67 and the middle sleeve body 64. Then, as shown in FIG. 10C, the first elastic wires 66 protrude and are deformed in an arc shape toward the outside in the radial direction (i.e., the wires 66 expand radially outwardly). However, at this point in time, the second elastic member 67 (second elastic wires) is not deformed.

The first elastic wires 66 are deformed while pushing and widening the opening edge portion of the foramen ovale O, so that the stick portion 2 which is provided in close vicinity of the first elastic wires 66 is center-aligned with respect to the foramen ovale O, and the stick portion 2 is positioned at the center of the foramen ovale O.

Figure 8:
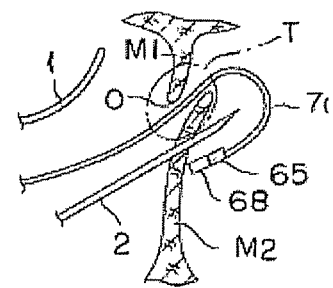
FIG. 8 is a cross-sectional schematic illustration of a state in which the foramen ovale valve is held and the needle portion is stuck into the foramen ovale valve.

Further, as shown in FIG. 10D, the main operation rod 7a is operated to move backward and when the rear end of the middle sleeve body 64 contact or engages the distal tip of the main tube 63, the first elastic wires 66 are not deformed so much and the second elastic wires 67 of the distal side deform in an arc shape toward the outside in the radial direction by the operation force. Consequently, as shown in FIG. 8, in the left atrium L, the contact member 68 and the distal tip sleeve body 65 approach the stick portion 2 (i.e., the contact member 68 and the distal tip sleeve body 65 bend back upon the remaining portion of the protruding operation member 7a as shown) so that the contact member 68 and the distal tip sleeve body 65 engage or contact the surface of the left atrium side of the foramen ovale valve M2. The contact member 68 and the distal tip sleeve body 65 hold the foramen ovale valve M2.

In this state, the operation lever 76b for the needle members 2a, 2a is moved forward until it contacts the lock mechanism 80. The stick portion 2 protrudes from the side portion of the catheter 30 through the operation member 7c and when the operation lever 76b for the needle is moved forward, it is possible to execute the sticking or puncture at a desirable or ideal position in the vicinity of the overlapping position of the atrial septum secundum M1 and the foramen ovale valve M2. On an occasion of this sticking, as shown in FIG. 8, a state exists in which the atrial septum secundum M1 and the foramen ovale valve M2 are located between the sandwich member 1 and the stick portion 2.

There is little concern that the position of the stick portion 2 will be deviated because the operation lever 76b for the needle contacts the lock mechanism 80. Also, when the stick portion 2 is stuck once, the position of the stick portion 2 is position-fixed with respect to the relation with the foramen ovale valve M2, that is, the positioning is carried out. Therefore, it is possible for the surgery operator to concentrate on the sandwiching operation with the sandwich member 1 without being overly concerned with the state of the stick portion 2, and so the sandwiching operation becomes easier.

Figure 9:
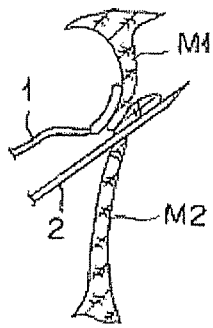
FIG. 9 is a cross-sectional schematic illustration of a state in which the foramen ovale valve and the atrial septum secundum are sandwiched by the needle portion and the sandwich member.
Figure 10:
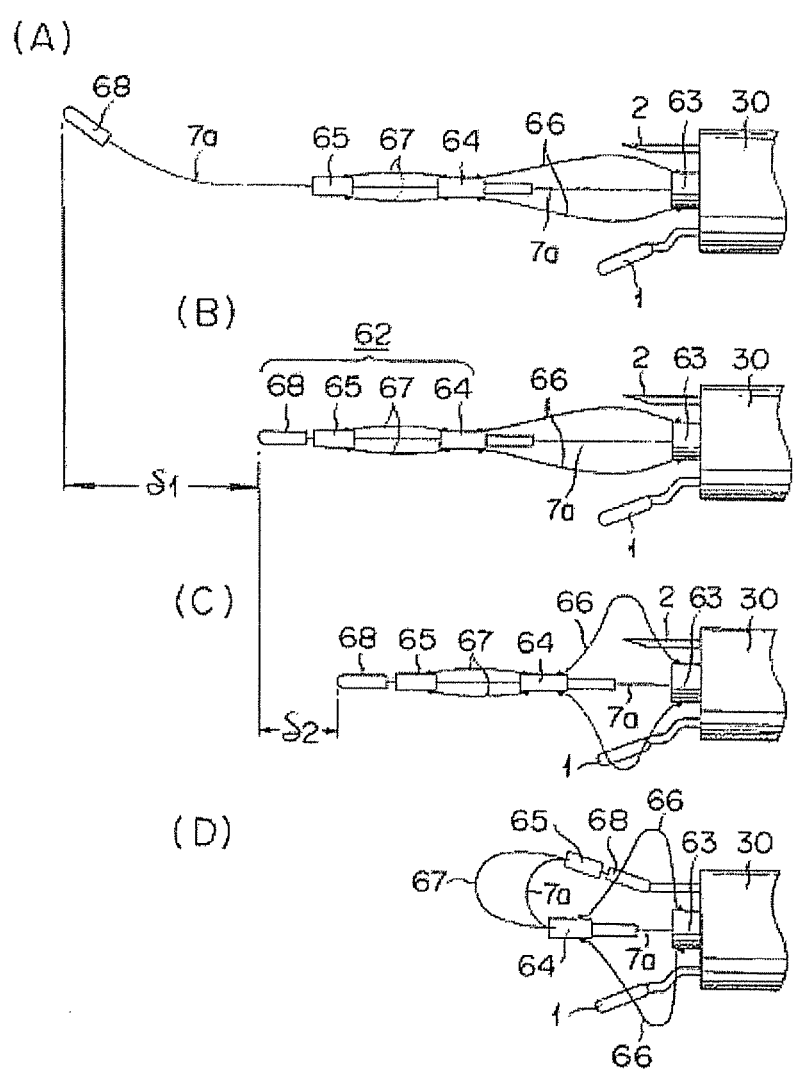
FIG. 10A to FIG. 10D are views showing operational states of the PFO closing device.

When the operation lever 76a for the sandwich member is moved forward, the sandwich member 1 protrudes from the distal tip of the catheter 30 through the operation member 7b, the sandwich member 1 presses the atrial septum secundum M1 toward the foramen ovale valve M2, and the atrial septum secundum M1 and the foramen ovale valve M2 are fixed or held in position in the wall thickness direction, that is in the forward/backward direction. As shown in FIG. 9, a state is produced in which the atrial septum secundum M1 and the foramen ovale valve M2 are positioned between the sandwich member 1 and the stick portion 2.

In this step, the main operation rod 7a is returned and, as shown in FIG. 10B, the first elastic wires 66 and the second elastic wires 67 are straightened out to take on a straight-line shape. Thereafter, the handle member 85 is operated to move backward, the main tube 63 is moved backward, and the whole positioning hold mechanism 60 is withdrawn in the lumen L5 of the catheter 30.

After this withdrawal, when the operation lever 76a for the sandwich member is operated so as to move backward and the sandwich member 1 is moved backward through the operation member 7b, the bend portion 1c of the sandwich member 1 is deformed by the end portion of the holder 50 (the bend portion of the sandwich member enters the lumen of the holder 50) so that the sandwich member approaches the stick portion 2 side and, as shown in FIG. 9, the atrial septum secundum M1 and the foramen ovale valve M2 are firmly sandwiched between the sandwich member 1 and the stick portion 2. The sandwich member 1, the positioning hold mechanism 60 and the stick portion 2 can respectively move independently, so that that the operation may not always be the sequence mentioned above. For example, it is also possible to perform the sticking operation to stick the foramen ovale valve M2 with the stick portion 2 after a state in which the sandwich member 1 is moved and the atrial septum secundum M1 is held by the sandwich member 1 and thereafter, the positioning hold mechanism 60 is operated and the atrial septum secundum M1 and the foramen ovale valve M2 are sandwiched by the sandwich member 1 and the positioning hold mechanism 60.

If the operation lever 76b for the needle members 2a, 2a is pressed to the lock mechanism 80 and a lock state is maintained, a sandwiching state of the atrial septum secundum M1 and the foramen ovale valve M2 caused by the sandwich member 1 and the stick portion 2 is maintained. By this lock, there is little concern that the stick portion 2 will be deviated, so that if the connection members 21a, 21b are fitted to the operation lever 76b for the needle members 2a, 2a and the operation lever 76a for the sandwich member 1, a predetermined electric current controlled by the control unit 22 flows from the operation lever 76b for the needle and the operation lever 76a for the sandwich member into the sandwich member 1 and the stick portion 2 through the operation members 7b, 7c. The atrial septum secundum M1 and the foramen ovale valve M2 are heated by the supply of this electric energy and joined or fused.

By controlling electric energy in the control unit 22, even if a portion of the sandwich member 1 and the stick member 2 is exposed in the blood, it is possible in this step to prevent the thrombus from being attached to the sandwich member 1 and the stick member 2. However, if a coating for preventing thrombus attachment is applied on the surfaces of the sandwich member 1 and the stick member 2, the attachment of the thrombus is prevented more certainly and is preferable.

When the heating is continued while maintaining a fusion temperature, the tissues of the atrial septum secundum M1 and the foramen ovale valve M2 melt and are mutually fused by an adhesive agent such as collagen, erastin and the like. With respect to the stick portion 2 of the present exemplified embodiment, the expanded plurality of needle members 2a, 2a contact the foramen ovale valve M2 over a relatively wide region, so that it is possible to sandwich the atrial septum secundum M1 and the foramen ovale valve M2 after sticking in a comparatively wide region and the fusion region of the biological tissue becomes wider.

When the fusion is completed, the energization is stopped, the operation lever 76b for the needle and the operation lever 76a for the sandwich member are moved backward and are housed in the guiding catheter 31. Then, if the guiding catheter 31 is pulled-out from the living body, the procedure is completed. It should be noted that after the procedure is completed, a very small hole remains on the foramen ovale valve M2 by the pulling-out of the stick portion 2, but it is healed afterward and bad influence such as generation of a thrombus and the like will not occur.

Figure 11:
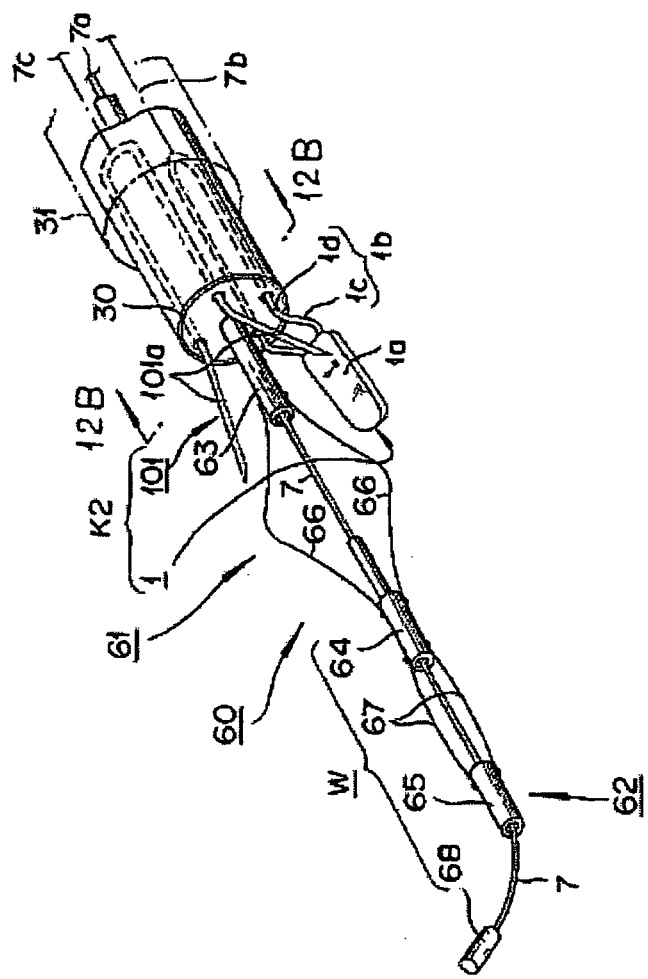
FIG. 11 is a perspective view of a main portion of a PFO closing device according to a second exemplified embodiment disclosed here.
Figure 12:
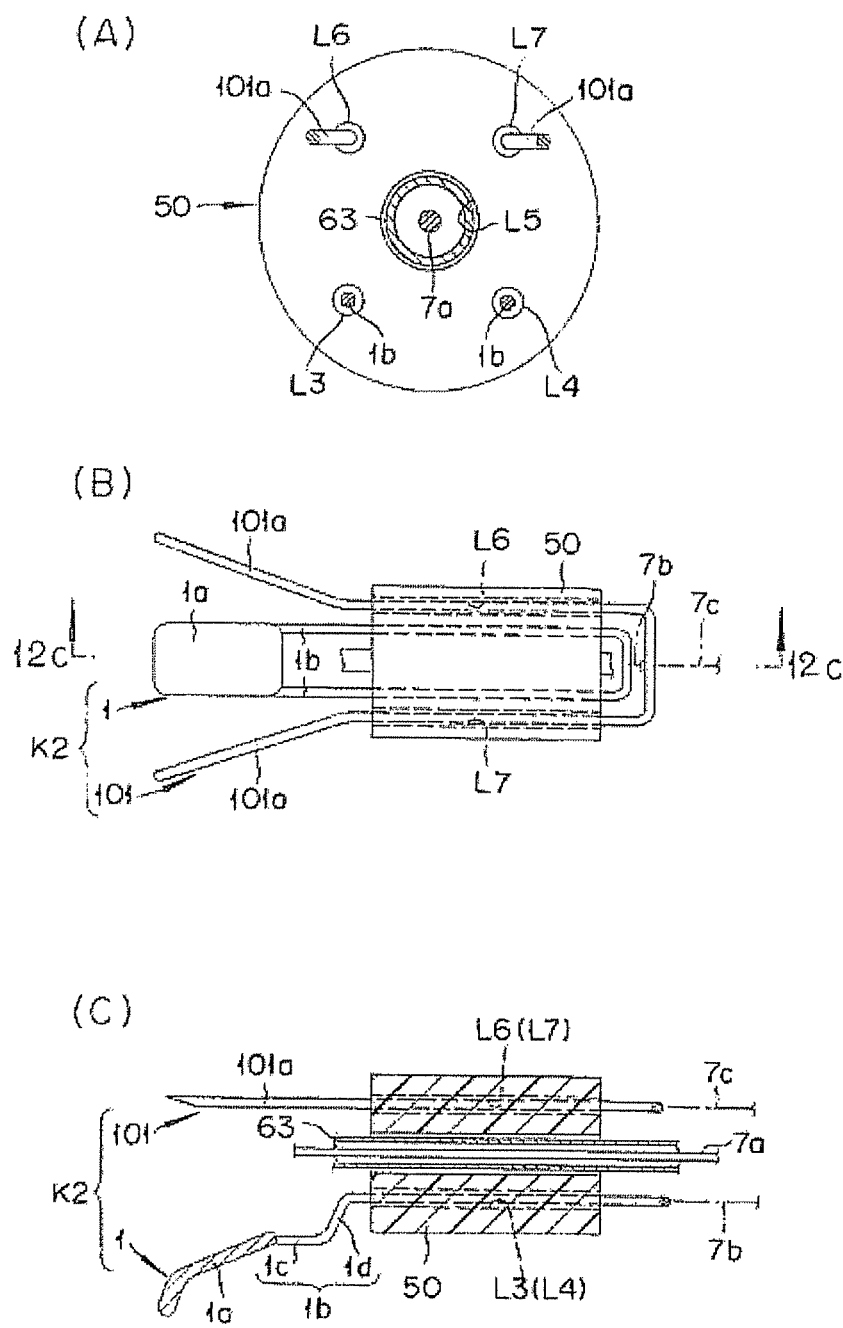
FIG. 12A is a cross-sectional view of the device taken along the section line 12A-12A in FIG. 11
FIG. 12B is a plan view of the portion of the device shown in FIG. 12A.
FIG. 12C is a cross-sectional view taken along the section line 12C-12C in FIG. 12B.

FIGS. 11-12 illustrate a PFO closing device according to a second exemplified embodiment. Features in this second embodiment of the closing device that are the same as those in the first embodiment are identified by the same reference numerals and a detailed discussion of such features is not repeated.

The PFO closing device according to this second exemplified embodiment differs from the first embodiment in terms of the stick portion 101 and the lumens L6, L7 for the stick portion.

As shown in FIGS. 11 and 12, the clamper K2 of the second exemplified embodiment is comprised of a sandwich member 1 for directly contacting one side of the atrial septum secundum M1 and a stick portion 101 to be stuck into the foramen ovale valve M2. The stick portion 101 is comprised of two elongated needle members 101a, 101a, both of which are formed in shapes expanding in a way of mutually widening (diverging away from one another) toward the distal direction. It should be noted, in the present exemplified embodiment, that both the needle members 101a, 101a are formed by bending them so that they possess a < shape, but it is also possible for them to be formed to be curved in arc shapes so they curve (diverge) away from one another in the distal direction.

The lumens L6, L7 for the stick portion extend in the axial direction of the catheter 30. Therefore, in a state in which both needle members 101a, 101a are housed in their respective lumens, the bends of both the needle members 101a, 101a are stretched (straightened out) by the elastic deformation and the needle members are in a state in which the expansion or widening of the needle members is eliminated. From this state, if the operation lever 76b for the needle members is operated and the needle members 101a, 101a protrude forwardly, the bends of both the needle members 101a, 101a are released by the elastic force and each of the needle members returns to a state in which it is expanded toward the distal side.

Also, if the operation lever 76b for the needle members is operated again and both the needle members 101a, 101a are pulled back into the lumen, the bends of both the needle members 101a, 101a are stretched (i.e., straightened out) by the elastic deformation and they assume a state in which the expansion or widening (divergence) is closed and they are housed in the lumens.

The PFO closing device according to the second exemplified embodiment exhibits operations and effects similar to those of the PFO closing device according to the first exemplified embodiment, and the expanded needle members 101a, 101a will contact with the foramen ovale valve M2 over a relatively wide region so that it is possible to sandwich the atrial septum secundum M1 and the foramen ovale valve M2 after the sticking in a wide region and it is possible to make the fusion region of the biological tissue larger. Also, it is possible to expand/shrink the needle members 101a, 101a (cause them to widen or move together) by simply moving the operation lever 76b forward and backward so that the operability thereof is quite good.

Here, it is also possible for the lumens L6, L7 of the second exemplified embodiment to be formed in shapes expanded in a way of widening toward the distal side in a manner similar to the lumens L1, L2 of the first exemplified embodiment. In addition, it is also possible for the needle members 101a, 101a which constitute the stick portion 101 to be provided by three or more pieces.

Figure 13:
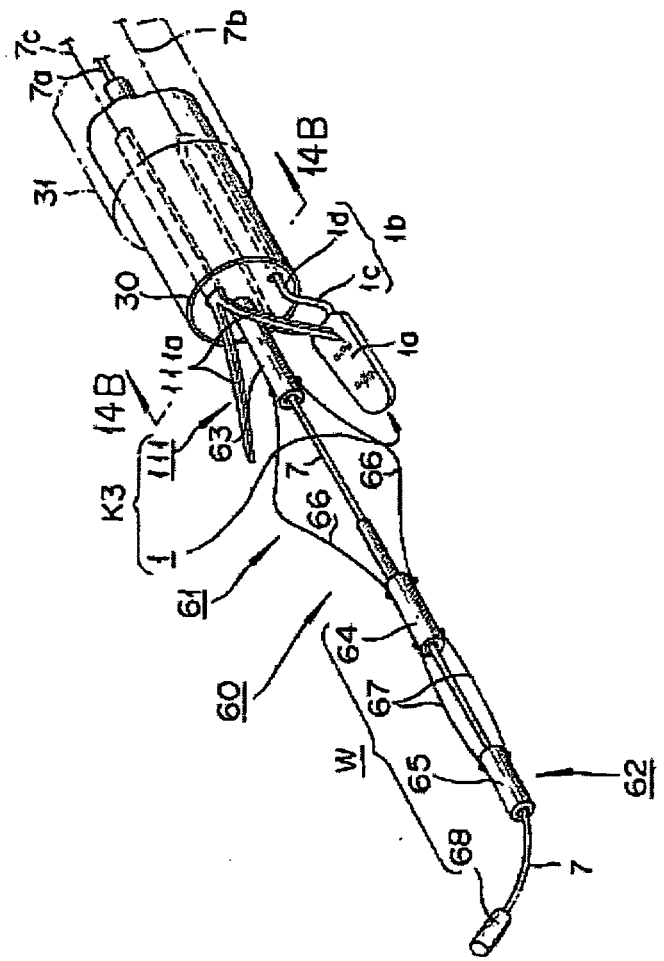
FIG. 13 is a perspective view of a main portion of a PFO closing device according to a third exemplified embodiment disclosed here.
Figure 14:
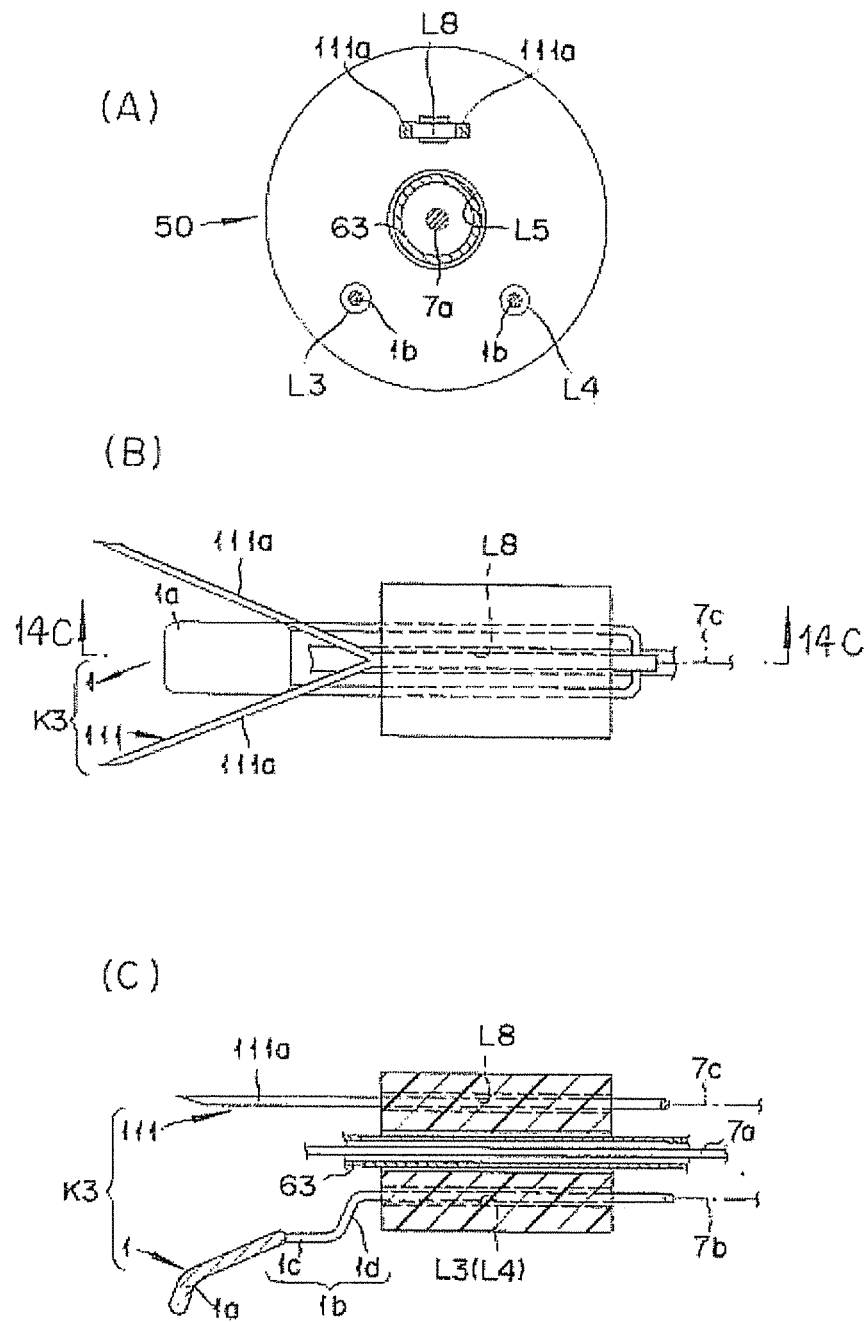
FIG. 14A is a cross-sectional view along the section line 14A-14A in FIG. 13.
FIG. 14B is a plan view of the portion of the device shown in FIG. 14A.
FIG. 14C is a cross-sectional view taken along the section line 14C-14C in FIG. 14B.

FIGS. 13-14 illustrate by way of example a third embodiment of the closing device. Features in this third embodiment of the closing device that are the same as those in the embodiments discussed above are identified by the same reference numerals and a detailed discussion of such features is not repeated.

The PFO closing device according to this third embodiment comprises a stick portion 111 and a lumen L8 for the stick portion that are different from those of the PFO closing device according to the first embodiment.

As shown in FIGS. 13 and 14, the clamper K3 of the third exemplified embodiment is comprised of a sandwich member 1 for directly contacting one side of the atrial septum secundum M1 and a stick portion 111 to be stuck into the foramen ovale valve M2. The distal side of the stick portion 111 branches into two pieces from a single piece, with the respective branch portions expanding (diverging) away from one another in the distal direction constituting needle members 111a, 111a.

The lumen L8 for the stick portion extends along the axial direction of the catheter 30, but it is also possible to form the lumen in a tilting (inclined) manner with respect to the axis of the catheter 30. In a state in which the stick portion 111 is housed in the lumen L8, the stick portion takes on a configuration in which the expansion (divergence) of the needle members 111a, 111a is closed by the elastic deformation, and if the operation lever 76b for the needle is operated from this state and the needle members 111a, 111a are moved in the distal direction to protrude distally out of the lumen L8, the force urging the needle members 111a, 111a together is removed and so the natural tendency for the needle members 111a, 111a to diverge away from one another is exhibited and the needle members 111a, 111a return to a state of expansion toward the distal side.

Also, if the operation lever 76b for the needle members 111a, 111a is operated again and both the needle members 111a, 111a are pulled back into the lumen L8, the natural and elastic divergence of the needle members 111a, 111a is overcome by the elastic deformation urging the needle members 111a, 111a towards each other, whereupon the state is once again realized in which the outward expansion of the needle members 111a, 111a is closed and they are housed in the lumen L8.

The PFO closing device according to the third exemplified embodiment exhibits operations and effects similar to those of the PFO closing device according to the first exemplified embodiment. The expanded needle members 111a, 111a will contact the foramen ovale valve M2 over a relatively wide region so that it is possible to sandwich the atrial septum secundum M1 and the foramen ovale valve M2 after the sticking in a wide region and so it is possible to make the fusion region of the biological tissue larger. Also, it is possible to expand/shrink the needle members 111a, 111a by simply moving the operation lever 76b for the needle forward and backward, so that the operability thereof is quite good.

It should be noted that the needle members 111a of the of the stick portion 111 of the third exemplified embodiment may be provided by two or more pieces. In addition, the stick portion 111 including the needle member 111a which is branched into a plurality of pieces may be provided by two or more pieces.

Figure 15:
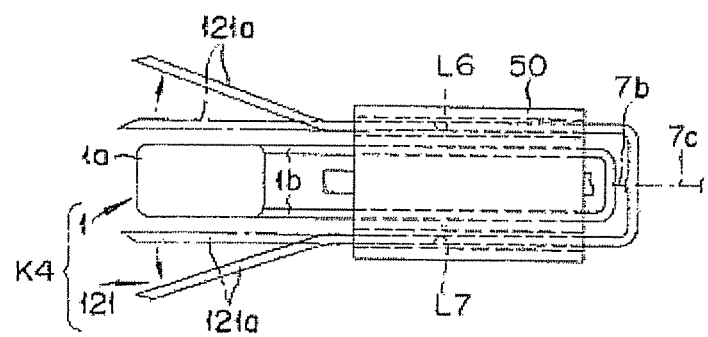
FIG. 15 is a plan view of a stick portion of the PFO closing device according to a fourth exemplified embodiment disclosed here.

FIG. 15 illustrates the stick portion of a PFO closing device according to a fourth exemplified embodiment. Features in this fourth embodiment of the closing device that are the same as those in the earlier described embodiments are identified by the same reference numerals and a detailed discussion of such features is not repeated.

The construction of the PFO closing device according to the fourth exemplified embodiment is similar to the PFO closing device according to the second exemplified embodiment, except for the stick portion 121.

As shown in FIG. 15, the clamper K4 of the fourth exemplified embodiment is comprised of a sandwich member 1 for directly contacting one side of the atrial septum secundum M1 and a stick portion 121 for penetrating or being stuck into the foramen ovale valve M2. The stick portion 121 of the fourth exemplified embodiment is constituted by two needle members 121a, 121a. Both of the needle members 121a, 121a are formed of a shape memory metal. By way of example, an Ni—Ti alloy can be sued for the shape memory metal. In the temperature of the environment of use (temperature in the body), both the needle members 121a, 121a possess straight shapes as shown by an alternate long and short dash line in FIG. 15 and are housed in the lumens L6, L7 in this state. The operation lever 76b for the needle members 121a, 121a is operated from this state and the needle members 121a, 121a are moved forward (distally. Thereafter, by heating the needle members 121a, 121a to a shape-recovery temperature, the needle members 121a, 121a are deformed into the stored shapes in which they expand or diverge (e.g., away from one another as illustrated) in the distal direction.

The heating of the needle members 121a, 121a is executed by supplying electric energy between the stick portion 121 and the sandwich member 1 from the electric energy supply unit 20. It should be noted that the amount of supply of the electric energy at that time is less than the energy necessary for fusing the biological tissue and, for example, the shape-recovery temperature is 40° and the temperature for fusing the biological tissue is 70°.

When the PFO closing device according to this embodiment is used, the foramen ovale valve M2 is held by the positioning hold mechanism 60 from the left atrium side and thereafter, the needle members 121a, 121a are moved forward (distally) to protrude distally from the catheter 30. Next, owing to the electric energy supply unit 20, electric energy is supplied between the stick portion 121 and the sandwich member 1, the stick portion 121 is heated to the shape-recovery temperature, and the needle members 121a, 121a of the stick portion 121 are expanded. Next, the lever 76b for the needle members 121a, 121a is moved forward and the needle members 121a, 121a are stuck into the aimed position of the foramen ovale valve M2. Thereafter, the atrial septum secundum M1 and the foramen ovale valve M2 are held between the sandwich member 1 and the stick portion 121, electric energy is supplied between the stick portion 121 and the sandwich member 1 by the electric energy supply unit 20, and the atrial septum secundum M1 and the foramen ovale valve M2 are thermally fused.

After the thermal fusion is completed, the expansion of the needle members 121a, 121a is closed (i.e., the needle members 121a, 121a are moved towards each other) by stopping the supply of the electric energy and lowering the temperature of the needle members 121a, 121a. The needle members 121a, 121a which have returned to the straight shapes are then stored in the catheter 30. Alternatively, it is also possible to close the expansion of the needle members 121a, 121a elastically (or plastically) and to store them by pulling the needle members 121a, 121 in the expanded state into the lumens L6, L7 of the catheter 30.

It should be noted in the present exemplified embodiment that the expansion of the needle members 121a, 121a of the stick portion 121 is executed before the sticking, but it is possible to execute the expansion before the thermal fusion after the sticking and according to circumstances, it is also possible to execute the sticking while expanding.

The PFO closing device according to the fourth exemplified embodiment exhibits operations and effects similar to those of the PFO closing device according to the first exemplified embodiment and the expanded needle members 121a, 121a will contact with the foramen ovale valve M2 in a relatively wide region, so that it is possible to sandwich the atrial septum secundum M1 and the foramen ovale valve M2 after the sticking in a wide region and it is possible to make the fusion region of the biological tissue larger. Also, it is possible for the heating of the stick portion 121 to use the electric energy supply unit 20 for the thermal fusion simultaneously, so that it is possible to employ the application easily without extending the equipment.

Here, it is also possible for the lumens L6, L7 of the fourth exemplified embodiment to be formed in shapes expanded in a manner widening toward the distal side similar to the lumens in the first exemplified embodiment. In addition, the needle members 121a which constitute the stick portion 121 can be provided three or more in number rather than the two illustrated needle members.

Figure 16:
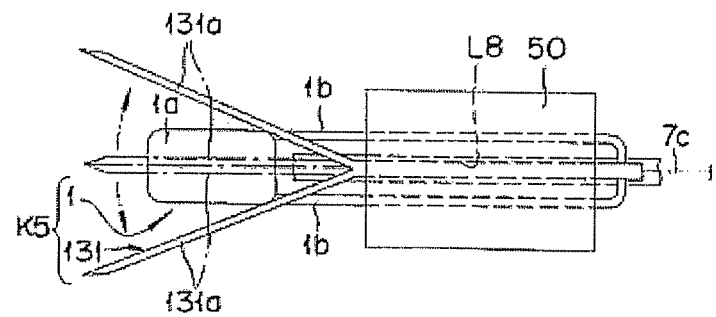
FIG. 16 is a plan view of a stick portion of a PFO closing device according to a fifth exemplified embodiment disclosed here.

FIG. 16 illustrates a stick portion of a PFO closing device according to a fifth exemplified embodiment. Features in this fifth embodiment of the closing device that are the same as those in the earlier described embodiments are identified by the same reference numerals and a detailed discussion of such features is not repeated.

The PFO closing device according to this fifth exemplified embodiment is similar to the PFO closing device according to the third exemplified embodiment, except for the stick portion 131.

Referring to FIG. 16, the clamper K5 of the fifth exemplified embodiment is comprised of a sandwich member 1 for directly contacting one side of the atrial septum secundum M1 and a stick portion 131 for being stuck into the foramen ovale valve M2. The distal side of the stick portion 131 branches into a plurality of pieces (two in the illustrated embodiment), and the respective branch portions constitute the needle members 131a, 131a. The needle members 131a, 131a (stick portion) is formed of a shape memory metal. There is used, for example, an Ni—Ti alloy for the shape memory metal. In the temperature of the environment of use (temperature in the body), both the needle members 131a, 131a are possess straight shapes as shown by an alternate long and short dash line in FIG. 16 and are housed or positioned in the lumen L8 in this state. The operation lever 76b for the needle members 131a, 131a is operated from this state so that the needle members 131a, 131a are distally moved to a protruding state. Thereafter, by heating the needle members 131a, 131a to a shape-recovery temperature, the needle members 131a, 131a are deformed into a shape in which they expand in the distal direction.

The heating of the needle members 131a, 131a is executed by supplying electric energy between the stick portion 131 and the sandwich member 1 from the electric energy supply unit 20. The amount of supply of electric energy at that time is less than the energy necessary for fusing the biological tissue. For example, the shape-recovery temperature is approximately 40° and the temperature for fusing the biological tissue is 70°.

When the PFO closing device according to this embodiment is used, the foramen ovale valve M2 is held by the positioning hold mechanism 60 from the left atrium side and thereafter, the lever 76b for the needle is operated and the needle members 131a, 131a are moved distally to protrude from the catheter 30. Next, from the electric energy supply unit 20, electric energy is supplied between the stick portion 131 and the sandwich member, the stick portion 131 is heated to the shape-recovery temperature and the needle members 131a, 131a of the stick portion 131 are expanded (diverge outwardly away from one another in the distal direction). Then, the lever 76b for effecting protrusion (distal movement) of the needle members is moved forward and the needle members 131a, 131a are stuck at (puncture) the aimed position of the foramen ovale valve M2. Thereafter, the atrial septum secundum M1 and the foramen ovale valve M2 are held between the sandwich member 1 and the stick portion 131, electric energy is supplied between the stick portion 131 and the sandwich member 1 by the electric energy supply unit 20, and the atrial septum secundum M1 and the foramen ovale valve M2 are thermally fused or joined.

After the thermal fusion is completed, the expansion of the needle members 131a, 131a is closed by stopping the supply of the electric energy and lowering the temperature of the needle members 131a, 131a, whereupon the needle members 131a, 131a are stored in the catheter 30. Alternatively, it is also possible to close the expansion of the needle members 131a, 131a elastically and to store them by pulling the needle members 131a, 131 of the expanded state into the lumen L8 of the catheter 30.

It should be noted in the present exemplified embodiment that the expansion of the needle members 131a, 131a of the stick portion 131 is executed before the sticking, but it is possible to execute the expansion before the thermal fusion after the sticking and according to circumstances, it is also possible to execute the sticking while expanding.

The PFO closing device according to the fifth exemplified embodiment exhibits operations and effects similar to those of the PFO closing device according to the first exemplified embodiment. The expanded needle members 131a, 131a are able to contact the foramen ovale valve M2 over a relatively wide range and so it is possible to sandwich the atrial septum secundum M1 and the foramen ovale valve M2 after the sticking over a relatively wide region and so it is possible to make the fusion region of the biological tissue larger. Also, it is possible for the heating of the stick portion 131 to use the electric energy supply unit 20 for the thermal fusion simultaneously, so that it is possible to employ the application easily without extending the equipment.

It should be noted that the needle members 131a, 131a of the stick portion of the fifth exemplified embodiment may be more in number than two. For example, the stick portion can be comprised of three or more pieces. In addition, the stick portion 131 including the needle members 131a, 131a which branch into a plurality of pieces may be provided by two or more pieces.

Figure 17:
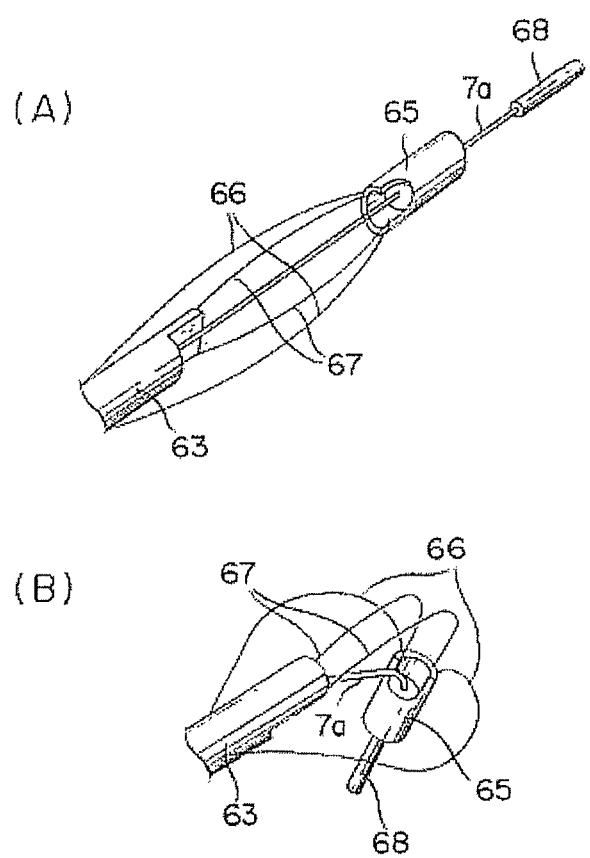

The positioning hold mechanism 60 in the above mentioned first to fifth exemplified embodiments is not limited by the illustrative embodiments mentioned above. For example, FIGS. 17(A) and 17(B) are illustrations of another example of the positioning hold mechanism. As shown in FIG. 17A, it is possible to provide the first elastic wire 66 and the second elastic wire 67 between the distal tip sleeve body 65 and the main tube 63 without providing the middle sleeve body 64. In this illustrative embodiment, when the main operation rod 7a is moved backward, as shown in FIG. 17B, the second elastic wire 67 is bent and deformed into an arc shape while the first elastic wire 66 protrudes and is deformed in an arc shape in the radial direction toward the outside direction. More specifically, the positioning of the stick portion 2 to the center of the foramen ovale O caused by the first elastic wire 66 and the holding of the foramen ovale valve M2 caused by the contact member 68 and the distal tip sleeve body 65 which are bent by the second elastic wire 67 are performed simultaneously based on one action caused by the backward movement of the main operation rod 7a.

The present invention is not limited only by aforementioned exemplified embodiments and it is possible for a person skilled in the art to employ various modifications within the technical concept of the present invention. In the exemplified embodiments mentioned above, it was explained that the disclosed embodiments of the closing device have useful application for closing a defect of PFO, but the device is not limited in that regard as the device is used as a biological tissue closing device applicable to various kinds of biological tissues. It is possible to use the device in case of closing a passway-shaped defect such as a left auricle closing device (Left Atrial Appendage) or in case of thermally necrosing a biological tissue in a predetermined region.

With respect to the PFO closing device of the exemplified embodiments, it is housed in a catheter and operates a clamper by the operation member, but it is not limited by this. For example, it is also possible to carry it until a predetermined position by employing a combination with a so-called catheter having a balloon.

Having described preferred embodiments of the invention with reference to the accompanying drawings, it is to be understood that the invention is not limited to those precise embodiments and that various changes and modifications could be effected therein, and equivalents employed, by one skilled in the art without departing from the spirit and scope of the invention as defined in the appended claims.

What is claimed is:

1. A biological tissue closing device comprising:
   a catheter;
   two needles movably positioned in a distal portion of the catheter to puncture biological tissue when the two needles project distally outside the catheter;
   the two needles each possessing a sharply pointed distal end, the two needles extending in a distal direction away from the catheter, the two needles diverging away from one another toward the distal ends of the two needles so that the sharply pointed distal ends of the two needles are spaced farther apart than portions of the two needles proximal of the sharply pointed distal ends;
   a sandwich member movably positioned in the distal portion of the catheter and cooperable with the two needles, when the sandwich member and the two needles project distally outside the catheter, to sandwich the biological tissue;
   each of the two needles being curved or bent in a direction away from the sandwich member;
   a first elongated operation member connected to the two needles to move the two needles relative to the catheter;
   a second elongated operation member operable independent of the first elongated operation member and connected to the sandwich member to move the sandwich member relative to the catheter;
   an electric energy supply unit electrically connectable to at least one of the two needles and the sandwich member to supply electric energy to both the at least one needle and the sandwich member;
   the sandwich member and the two needles cooperating with one another, while the biological tissue is punctured by the at least one needle, to clamp the biological tissue and fuse together the biological tissue by supplying electric energy from the electric energy supply unit to the sandwich member and the at least one needle.

2. The biological tissue closing device according to claim 1, wherein the first elongated operation member extends through an interior of the catheter and is connected to a first operation lever which is operable by a user to move the two needles, and wherein the second elongated operation member extends through the interior of the catheter and is connected to a second operation lever which is operable by the user to move the sandwich member.

3. A biological tissue closing device comprising:
   a clamper comprised of two needles positioned at a distal portion of a catheter and each possessing a sharply pointed distal end configured to puncture biological tissue, and a sandwich member for sandwiching the biological tissue in cooperation with the two needles when the two needles puncture the biological tissue;
   the two needles extending in a distal direction away from the catheter, the two needles diverging away from one another toward the distal ends of the two needles so that the sharply pointed distal ends of the two needles are spaced farther apart than portions of the two needles proximal of the sharply pointed distal ends;
   each of the two needles being curved or bent in a direction away from the sandwich member;
   an electric energy supply unit electrically connectable to the clamper to supply electric energy to the clamper;
   at least one of the two needles and the sandwich member both constituting electrodes connectable to the electric energy supply unit;
   the two needles and the sandwich member being movable relative to one another to clamp the biological tissue between the two needles and the sandwich member to fuse together the biological tissue by supplying electric energy from the electric energy supply unit to the at least one needle and the sandwich member;
   the two needles and the sandwich member being independently movable with respect to the catheter.

4. The biological tissue closing device according to claim 3, wherein the catheter possesses an axis, and the two needles are transversely arranged relative to the axis of the catheter.

5. The biological tissue closing device according to claim 3, wherein the catheter possesses an axis, and comprising a holder at a distal portion of the catheter, the holder being provided with two lumens transversely oriented relative to the axis of the catheter, each of the elongated two needles being movably positioned in a respective one of the two lumens and being deformed elastically as each of the two needles is moved into and out of the respective one of the two lumens.

6. The biological tissue closing device according to claim 3, wherein the two needles diverge away from each other in a distal direction during forward movement and converge toward one another during backward movement.

7. The biological tissue closing device according to claim 6, wherein the catheter possesses an axis, and further comprising a holder at a distal portion of the catheter, the holder being provided with a plurality of lumens, each of the two needles being movably positioned in one of the two lumens, each lumen of the two lumens possessing a shape such that the two lumens diverge outwardly away from one another in the distal direction.

8. The biological tissue closing device according to claim 6, wherein each of the two needles possesses a shape such that the two needles expand mutually outwardly away from one another toward the distal direction when in a protruding state, and the two needles in a retracted state relative to the protruding state are housed in the holder and diverge less than in the protruding state.

9. The biological tissue closing device according to claim 6, wherein the biological tissue closing device is used in an environment of use, wherein the two needles are made of a shape memory material, and the two needles expand outwardly away from each other by a shape-recovery temperature higher than a temperature of the environment of use.

10. The biological tissue closing device according to claim 9, wherein the two needles made of the shape memory material are heated to the shape-recovery temperature by supplying electric energy from the electric energy supply unit to the two needles.

11. The biological tissue closing device according to claim 6, wherein the biological tissue closing device is used in an environment of use, wherein the two needles are made of a shape memory material and possesses a distal tip branching into a plurality of branch portions each constituting one of the two needles, the two needles being held in a state in which the branch portions are relatively more closely positioned at the temperature of the environment of use, and the branch portions mutually expanding way from each other toward the distal direction by a shape-recovery temperature higher than the temperatures of the environment of use.

12. The biological tissue closing device according to claim 3, wherein the two needles are deformed, before clamping the biological tissue, in a direction away from the sandwich member.

13. The biological tissue closing device according to claim 3, wherein the catheter is guided by a guiding catheter whose distal portion is bent to direct the distal portion to an opening portion formed at the biological tissue.

14. The biological tissue closing device according to claim 3, wherein the biological tissue closing device is provided at the proximal portion of the catheter with an operation unit for operating the clamper, and the operation unit and the clamper are coupled by an operation member inserted into the catheter.

15. The biological tissue closing device according to claim 3, wherein the two needles and the sandwich member are each connected to a respective elongated wire extending through an interior of the catheter, with each wire connected to a respective operation lever operable by a user to move the two needles and the sandwich member independently of one another.

16. A method for joining together biological tissue to close an opening comprising:
clamping biological tissue between two needles and a sandwich member positioned at a distal end of a catheter, the two needles and the sandwich member being mounted at a distal end portion of a catheter and being independently movable relative to the catheter, the two needles each possessing a sharply pointed distal end, the two needles extending in a distal direction away from the catheter, the two needles diverging away from one another toward the distal ends of the two needles so that the sharply pointed distal ends of the two needles are spaced farther apart than portions of the two needles proximal of the sharply pointed distal ends, each of the two needles being curved or bent in a direction away from the sandwich member;
penetrating the biological tissue with the two needles by distally moving the two needles relative to the catheter so that the two needles penetrate the biological tissue; and
supplying energy to the sandwich member and at least one of the two needles as the biological tissue is clamped between the two needles and the sandwich member to fuse together the biological tissue.

17. The method according to claim 16, wherein the two needles penetrate the biological tissue before clamping the biological tissue.

18. The method according to claim 17, further comprising forwardly moving the two needles relative to the catheter so that the two needles distally protrude from the catheter, the two needles diverging away from one another during the forward movement.

19. The method according to claim 17, further comprising forwardly moving the two needles relative to the catheter so that the two needles distally protrude from the catheter, the two needles being made of a shape memory material, and the energy being applied to the two needles to heat the two members needles to a temperature above a shape memory temperature to cause the two needles to diverage away from one another in the distal direction.

20. The method according to claim 16, wherein the energy is supplied to the two needles and the sandwich member while the two needles are penetrating the biological tissue so that the two needles pass through the biological tissue.

21. A biological tissue closing device comprising:
a pair of needles positioned at a distal portion of a catheter and each possessing a sharply pointed distal end for puncturing biological tissue, the pair of needles extending in a distal direction away from the catheter and diverging away from one another toward the distal ends so that the sharply pointed distal ends of the pair of needles are spaced farther apart than portions of the pair of needles proximal of the sharply pointed distal ends;
a sandwich member for sandwiching the biological tissue in cooperation with the pair of needles during puncturing of the biological tissue;
each of the pair of needles being curved or bent in a direction away from the sandwich member;
an electric energy supply unit electrically connectable to the pair of needles and the sandwich member to supply electric energy to the pair of needles and the sandwich member;
the pair of needles and the sandwich member being movable relative to one another to clamp the biological tissue between the sandwich member and the pair of needles to fuse together the biological tissue by supplying electric energy from the electric energy supply unit to the pair of needles and the sandwich member; and
the pair of needles and the sandwich member being independently movable with respect to the catheter.

* * * * *